(12) United States Patent
Chen et al.

(10) Patent No.: US 6,995,168 B2
(45) Date of Patent: Feb. 7, 2006

(54) TRIAZASPIRO COMPOUNDS USEFUL FOR TREATING OR PREVENTING PAIN

(75) Inventors: Zhengming Chen, Belle Mead, NJ (US); Sam Victory, Newtown, PA (US)

(73) Assignee: Euro-Celtique S.A. (LU)

( * ) Notice: Subject to any disclaimer, the term of this patent is extended or adjusted under 35 U.S.C. 154(b) by 82 days.

(21) Appl. No.: 10/448,627

(22) Filed: May 29, 2003

(65) Prior Publication Data

US 2005/0009854 A1 Jan. 13, 2005

Related U.S. Application Data

(60) Provisional application No. 60/460,219, filed on Apr. 3, 2003, and provisional application No. 60/384,807, filed on May 31, 2002.

(51) Int. Cl.
*A61K 31/438* (2006.01)
*C07D 401/04* (2006.01)

(52) U.S. Cl. .......................... 514/278; 546/18
(58) Field of Classification Search ................ 546/18; 514/278
See application file for complete search history.

(56) References Cited

U.S. PATENT DOCUMENTS

| | | | |
|---|---|---|---|
| 3,161,644 A | | 12/1964 | Janssen et al. |
| 3,238,216 A | * | 3/1966 | Janssen ................. 546/20 |
| 3,536,809 A | | 10/1970 | Applezweig et al. |
| 3,598,123 A | | 8/1971 | Zaffaroni |
| 3,845,770 A | | 11/1974 | Theeuwes et al. |
| 3,916,899 A | | 11/1975 | Theeuwes et al. |
| 4,008,719 A | | 2/1977 | Theeuwes et al. |
| 4,374,245 A | | 2/1983 | Davis et al. |
| 4,409,230 A | | 10/1983 | Davis et al. |
| 4,418,067 A | | 11/1983 | Davis et al. |
| 5,059,595 A | | 10/1991 | Le Grazie |
| 5,073,543 A | | 12/1991 | Marshall et al. |
| 5,120,548 A | | 6/1992 | McClelland et al. |
| 5,354,556 A | | 10/1994 | Sparks et al. |
| 5,591,767 A | | 1/1997 | Mohr et al. |
| 5,639,476 A | | 6/1997 | Oshlack et al. |
| 5,674,533 A | | 10/1997 | Santus et al. |
| 5,698,155 A | | 12/1997 | Grosswald et al. |
| 5,733,566 A | | 3/1998 | Lewis |
| 5,739,336 A | | 4/1998 | Weinhardt et al. |
| 5,789,402 A | | 8/1998 | Audia et al. |
| 5,807,865 A | | 9/1998 | Harrison et al. |
| 5,852,029 A | | 12/1998 | Fisher |
| 6,060,482 A | | 5/2000 | Heine et al. |
| 6,277,991 B1 | | 8/2001 | Hohlweg et al. |
| 6,362,203 B1 | | 3/2002 | Mogi et al. |
| 6,686,370 B2 | | 2/2004 | Kyle et al. |

FOREIGN PATENT DOCUMENTS

| | | |
|---|---|---|
| EP | 0 921 125 A1 | 6/1998 |
| EP | 0 856 514 A1 | 8/1998 |
| WO | WO 99/45011 A1 | 9/1999 |
| WO | WO 99/59997 A1 | 11/1999 |
| WO | WO 00/06545 A1 | 2/2000 |
| WO | WO 01/07050 A1 | 2/2001 |
| WO | WO 01/36418 A1 | 5/2001 |
| WO | WO 01/39723 A2 | 6/2001 |

OTHER PUBLICATIONS

Caplus English Abstract DN 78:3415 Saucin et al 1972.*
Caplus English Abstract DN 60:90893 BE 633914 Jansen C. 1963.*
Gorissen et al.. Differentiation of solubilized dopamine receptors from spirodecanone binding sites in rat striatum. FEBS Lett. 1980 Nov. 17;121(1):133–8.
Saucin et al., Caplus English Abstract DN 78:3415, 1972.
Jansen C., Caplus English Abstract DN 60:90893 BE 633914, 1963.
Wittenberg et al., J. Org. Chem. 1993, 58:4139–4141.
Gropp et al. Protection against hypoxia–reoxygenation in the absence of poly (ADP–ribose) synthetase in isolated working hearts. J Mol Cell Cardiol. 1999 Jan.; 31(1):297–303.

* cited by examiner

*Primary Examiner*—Rita Desai
(74) *Attorney, Agent, or Firm*—Jones Day

(57) ABSTRACT

Triazaspiro Compounds, compositions comprising a Triazaspiro Compound, methods for treating or preventing pain in an animal comprising administering to an animal in need thereof an effective amount of a Triazaspiro Compound and methods for stimulating opioid-receptor function in a cell comprising contacting a cell capable of expressing an opioid receptor with an effective amount of a Triazaspiro Compound are disclosed.

44 Claims, No Drawings

TRIAZASPIRO COMPOUNDS USEFUL FOR TREATING OR PREVENTING PAIN

This application claims the benefit of U.S. provisional application No. 60/384,807, filed May 31, 2002, and of U.S. provisional application No. 60/460,219, filed Apr. 3, 2003, the disclosure of each of which is incoporated by reference in its entirety.

1. FIELD OF THE INVENTION

The present invention relates to Triazaspiro Compounds, compositions comprising a Triazaspiro Compound and methods for preventing or treating pain in an animal in need thereof comprising administering to the animal an effective amount of a Triazaspiro Compound.

2. BACKGROUND OF THE INVENTION

Pain is the most common symptom for which patients seek medical advice and treatment. Pain can be acute or chronic. While acute pain is usually self-limited, chronic pain can persist for 3 months or longer and lead to significant changes in a patient's personality, lifestyle, functional ability or overall quality of life (K. M. Foley, *Pain, in Cecil Textbook of Medicine* 100–107 (J. C. Bennett and F. Plum eds., 20th ed. 1996).

Pain has been traditionally managed by administering a non-opioid analgesic, such as acetylsalicylic acid, choline magnesium trisalicylate, acetaminophen, ibuprofen, fenoprofen, diflusinal and naproxen; or an opioid analgesic, including morphine, hydromorphone, methadone, levorphanol, fentanyl, oxycodone and oxymorphone. Id.

U.S. Pat. No. 3,238,216 to Janssen et al. discloses particular spirocompounds allegedly useful as neuroleptic, including analgesic, agents.

International Publication No. WO 99/45011 by Janssen Pharmaceutica N.V. discloses particular spirocompounds allegedly useful for the treatment of pain.

U.S. Pat. No. 6,277,991 to Hohlweg et al. discloses particular spirocompounds allegedly useful for the treatment of migraine headache.

Traditional non-opioid analgesics exert their pharmacological activity once they have passed through the blood-brain barrier. But this blood-brain barrier passage can lead to many undesirable central nervous system-mediated side effects, such as respiratory depression, increased drug-abuse potential, increased drug tolerance, increased drug dependence, constipation and unwanted euphoria.

U.S. Pat. No. 6,362,203 to Mogi et al. discloses particular 4-hydroxy-4-phenylpiperidine compounds allegedly useful as peripheral analgesic agents.

There remains a clear need in the art for new drugs useful for treating or preventing pain and that reduce or avoid one or more side effects associated with traditional therapy for treating pain.

Citation of any reference in Section 2 of this application is not to be construed as an admission that such reference is prior art to the present application.

3. SUMMARY OF THE INVENTION

The present invention encompasses compounds having the formula (Ia):

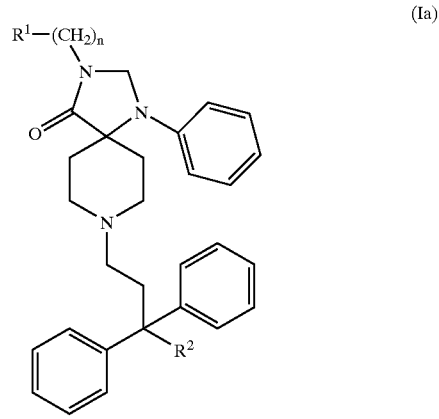

(Ia)

and pharmaceutically acceptable salts thereof, wherein:

$R^1$ is hydrogen, —COOH, —COOR$^3$, —C(O)NH$_2$, —C(O)NH(C$_1$–C$_4$ alkyl), —C(O)N(C$_1$–C$_4$ alkyl)(C$_1$–C$_4$ alkyl), —CN, —N(H)S(O)$_2$(C$_1$–C$_4$ alkyl), or

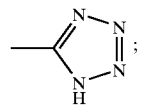

$R^2$ is —COOH, —COOR$^3$ or

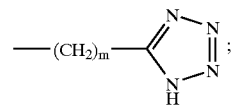

$R^3$ is —(C$_1$–C$_6$ alkyl), benzyl, phenyl, or —(C$_3$–C$_6$ cycloalkyl);

n is 0 when $R^1$ is hydrogen, and n is an integer ranging from 1 to 4 when $R^1$ is other than hydrogen; and m is an integer ranging from 0 to 4.

The present invention also encompasses compounds having the formula (Ib):

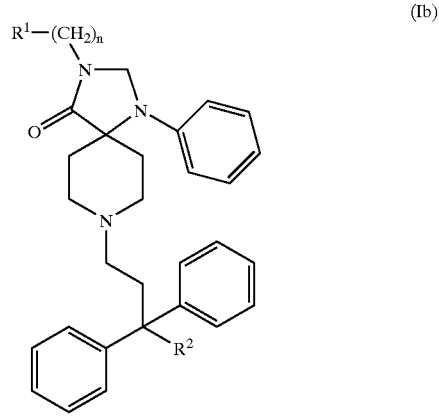

(Ib)

and pharmaceutically acceptable salts thereof, wherein:

$R^1$ is —COOH, —COOR$^3$, —C(O)NH$_2$, —C(O)NH(C$_1$–C$_4$ alkyl), —C(O)N(C$_1$–C$_4$ alkyl)(C$_1$–C$_4$ alkyl), —CN, —N(H)S(O)$_2$(C$_1$–C$_4$ alkyl), or

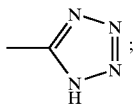

$R^2$ is —COOH, —COOR$^3$, —C(O)N(CH$_3$)$_2$ or

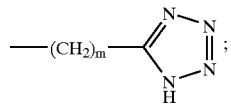

$R^3$ is —(C$_1$–C$_6$ alkyl), benzyl, phenyl, or —(C$_3$–C$_6$ cycloalkyl);

n is an integer ranging from 1 to 4; and m is an integer ranging from 0 to 4.

The present invention also encompasses compounds having the formula (Ic):

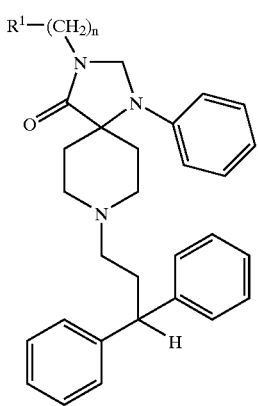

(Ic)

and pharmaceutically acceptable salts thereof, wherein:

$R^1$ is —COOH, —C(O)NH$_2$, —C(O)NH(C$_1$–C$_4$ alkyl), —C(O)N(C$_1$–C$_4$ alkyl)(C$_1$–C$_4$ alkyl), —N(H)S(O)$_2$(C$_1$–C$_4$ alkyl), or

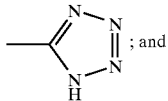; and n is an integer ranging from 1 to 4.

A Triazaspiro Compound is useful for treating or preventing pain in an animal.

The invention also relates to compositions comprising an effetive amount of a Triazaspiro Compound and a pharmaceutically acceptable carrier or excipient. The present compositions are useful for treating or preventing pain in an animal.

The invention also relates to kits comprising a container containing a Triazaspiro Compound, and instructions for its use.

The invention further relates to methods for preventing pain in an animal, comprising administering to an animal in need thereof an effective amount of a Triazaspiro Compound.

The invention further relates to methods for treating pain in an animal, comprising administering to an animal in need thereof an effective amount of a Triazaspiro Compound.

The invention still further relates to methods for stimulating opioid-receptor function in a cell, comprising contacting a cell capable of expressing an opioid receptor with an effective amount of a Triazaspiro Compound.

In a still further embodiment, the present invention is directed toward a method for preparing a composition, comprising the step of admixing a Triazaspiro Compound and a pharmaceutically acceptable carrier or excipient.

The present invention may be understood more fully by reference to the following detailed description and illustrative examples, which are intended to exemplify non-limiting embodiments of the invention.

4. DETAILED DESCRIPTION OF THE INVENTION

4.1 Definitions

As used herein, the terms used above having following meaning:

A "Triazaspiro Compound" is a compound of formula (Ia), formula (Ib) or formula (Ic), a compound set forth in Section 4.3 of this application, or a pharmaceutically acceptable salt of any of the above.

"—C$_1$–C$_4$ alkyl" means a straight or branched non-cyclic hydrocarbon chain having from 1 to 4 carbon atoms. Representative straight chain —C$_1$–C$_4$ alkyls include -methyl, -ethyl, -n-propyl, and -n-butyl. Representative branched chain —C$_1$–C$_4$ alkyls include -isopropyl, -sec-butyl, -isobutyl, and -tert-butyl.

"—C$_1$–C$_6$ alkyl" means a straight or branched non-cyclic hydrocarbon chain having from 1 to 6 carbon atoms. Representative straight chain —C$_1$–C$_6$ alkyls include -methyl, -ethyl, -n-propyl, -n-butyl, -n-pentyl and-n-hexyl. Representative branched chain —C$_1$–C$_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl and 3,3-dimethylbutyl.

"—C$_3$–C$_6$ cycloalkyl" means a saturated cyclic hydrocarbon having from 3 to 6 carbon atoms. Representative —C$_3$–C$_6$ cycloalkyls are -cyclopropyl, -cyclobutyl, -cyclopentyl and cyclohexyl.

The term "animal," includes, but is not limited to, a cow, monkey, horse, sheep, pig, chicken, turkey, quail, cat, dog, mouse, rat, rabbit, guinea pig and human.

The phrase "pharmaceutically acceptable salt," as used herein, is a salt formed from an acid and the basic nitrogen group of a Triazaspiro Compound. Such salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt of a Triazaspiro Compound having an acidic functional group, such as a carboxylic acid functional group, and a pharmaceutically acceptable inorganic or organic base. Suitable bases include, but are not limited to, hydroxides of alkali metals such as sodium, potassium and lithium; hydroxides of alkaline earth metal such as calcium and magnesium; hydroxides of other metals, such as aluminum and zinc; ammonia; and organic amines, such as unsubstituted or hydroxy-substituted mono-, di-, or trialkylamines; dicyclohexylamine; tributylamine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl) methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "treatment of" and "treating" pain includes the amelioration or cessation of pain.

The phrase "prevention of" and "preventing" pain includes the avoidance of the onset of pain.

The phrase "opioid receptor" means a δ-opioid receptor, a κ-opioid receptor, a μ-opioid receptor or an ORL-1 receptor.

The phrase "effective amount" when used in connection with a Triazaspiro Compound means an amount effective for (a) treating or preventing paint, or (b) stimulating opioid receptor function in a cell.

The phrase "effective amount" when used in connection with another therapeutic agents means an amount for providing the therapeutic effect of the therapeutic agent.

When a first group is "substituted with one or more" second groups, one or more hydrogen atoms of the first group is replaced with a corresponding number of second groups. When the number of second groups is two or greater, the second groups can be the same or different. In one embodiment, the number of second groups is 1 or 2. In another embodiment, the number of second groups is 1.

4.2 The Triazaspiro Compounds of Formulas (Ia)–(Ic)

4.2.1 The Triazaspiro Compounds of Formula (Ia)

As stated above, the present invention encompasses Triazaspiro Compounds having the formula (Ia):

(Ia)

and pharmaceutically acceptable salts thereof, wherein:

$R^1$ is hydrogen, —COOH, —COOR$^3$, —C(O)NH$_2$, —C(O)NH(C$_1$–C$_4$ alkyl), —C(O)N(C$_1$–C$_4$ alkyl)(C$_1$–C$_4$ alkyl), —CN, —N(H)S(O)$_2$(C$_1$–C$_4$ alkyl), or $R^2$ is —COOH, —COOR$^3$ or —(CH$_2$)$_m$—

$R^3$ is —(C$_1$–C$_6$ alkyl), benzyl, phenyl, or —(C$_3$–C$_6$ cycloalkyl);

n is 0 when $R^1$ is hydrogen, and n is an integer ranging from 1 to 4 when $R^1$ is other than hydrogen; and m is an integer ranging from 0 to 4.

In one embodiment, the Triazaspiro Compounds of formula (Ia) are those wherein $R^1$ is hydrogen and n is 0.

In another embodiment, the Triazaspiro Compounds of formula (Ia) are those whrein $R^1$ is other than hydrogen and n is an integer ranging from 1 to 4.

In another embodiment, the Triazaspiro Compounds of formula (Ia) are those wherein $R^1$ is —COOH or —COOR$^3$, and $R^3$ is —(C$_1$–C$_6$ alkyl), benzyl, phenyl, or —(C$_3$–C$_6$ cycloalkyl). In another embodiment, $R^3$ is —CH$_3$.

In another embodiment, the Triazaspiro Compounds of of formula (Ia) are those wherein $R^1$ is —C(O)NH$_2$, —C(O)NH(C$_1$–C$_4$ alkyl) or —C(O)N(C$_1$–C$_4$ alkyl)(C$_1$–C$_4$ alkyl). In another embodiment, $R^1$ is —C(O)NH(CH$_3$) or —C(O)N(CH$_3$)$_2$.

In another embodiment, the Triazaspiro Compounds of formula (Ia) are those wherein $R^1$ is —CN.

In another embodiment, the Triazaspiro Compounds of formula (Ia) are those wherein $R^1$ is —N(H)S(O)$_2$(C$_1$–C$_4$ alkyl). In another embodiment, $R^1$ is —N(H)S(O)$_2$(CH$_3$).

In another embodiment, the Triazaspiro Compounds of formula (Ia) are those wherein $R^1$ is In another embodiment, the Triazaspiro Compounds of formula (Ia) are those wherein $R^2$ is —COOH or —COOR$^3$, and $R^3$ is —(C$_1$–C$_6$ alkyl), benzyl, phenyl, or —(C$_3$–C$_6$ cycloalkyl). In another embodiment, $R^3$ is —CH$_3$.

In another embodiment, t the Triazaspiro Compounds of formula (Ia) are those wherein $R^2$ is —(CH$_2$)$_m$—

In another embodiment, m is 0 or 1. In another embodiment, m is 0.

In another embodiment, the Triazaspiro Compounds of formula (Ia) are those wherein $R^1$ is H, n is 0, and $R^2$ is —COOR$^3$, and $R^3$ is —(C$_1$–C$_6$ alkyl), benzyl, phenyl, or —(C$_3$–C$_6$ cycloalkyl). In another embodiment, $R^3$ is —CH$_3$.

In another embodiment, the Triazaspiro Compounds of formula (Ia) are those wherein $R^1$ is H, n is 0, $R^2$ is

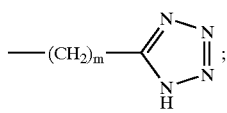

and m is 0.

Illustrative Triazaspiro Compounds of formula (Ia) are:

Compound AC

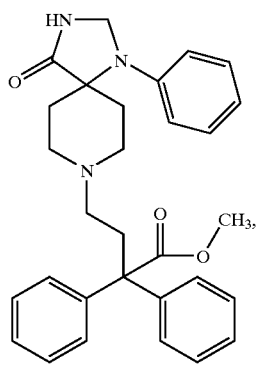

4-(4-Oxo-1-phenyl-1,3,8-triaza-spiro[4.5]dec-8-yl)-2,2-diphenyl-butyric acid methyl ester;

Compound AF

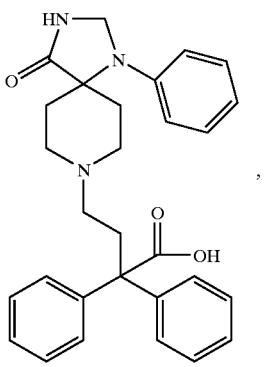

4-(4-Oxo-1-phenyl-1,3,8-triaza-spiro[4.5]dec-8-yl)-2,2-diphenyl-butyric acid;

Compound AK

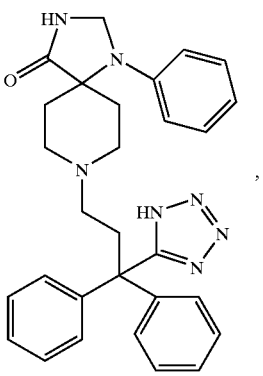

8-[3,3-Diphenyl-3-(1H-tetrazol-5-yl)-propyl]-1-phenyl-1,3,8-triaza-spiro[4.5]decan-4-one;

and pharmaceutically acceptable salts thereof.

4.2.2 The Triazaspiro Compounds of Formula (Ib)

The present invention also encompasses Triazaspiro Compounds having the formula (Ib):

(Ib)

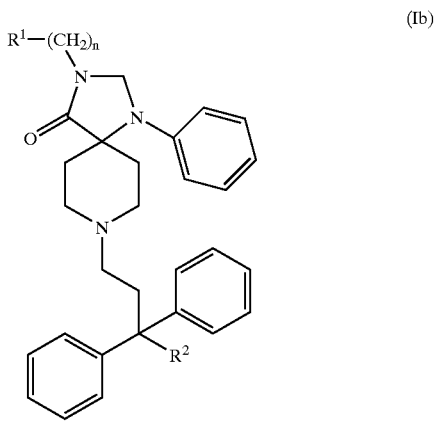

and pharmaceutically acceptable salts thereof, wherein:

$R^1$ is —COOH, —COOR$^3$, —C(O)NH$_2$, —C(O)NH(C$_1$–C$_4$ alkyl), —C(O)N(C$_1$–C$_4$ alkyl)(C$_1$–C$_4$ alkyl), —CN, —N(H)S(O)$_2$(C$_1$–C$_4$ alkyl), or

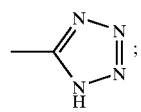

$R^2$ is —COOH, —COOR$^3$, —C(O)N(CH$_3$)$_2$, or

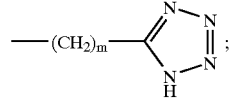

$R^3$ is —(C$_1$–C$_6$ alkyl), benzyl, phenyl, or —(C$_3$–C$_6$ cycloalkyl);

n is an integer ranging from 1 to 4; and m is an integer ranging from 0 to 4.

In one embodiment, the Triazaspiro Compounds of formula (Ib) are those wherein $R^1$ is —COOH or —COOR$^3$, and $R^3$ is —(C$_1$–C$_6$ alkyl), benzyl, phenyl, or —(C$_3$–C$_6$ cycloalkyl). In one embodiment, $R^3$ is —CH$_3$.

In another embodiment, the Triazaspiro Compounds of formula (Ib) are those wherein $R^1$ is —C(O)NH$_2$, —C(O)NH(C$_1$–C$_4$ alkyl), or —C(O)N(C$_1$–C$_4$ alkyl)(C$_1$–C$_4$ alkyl). In another embodiment, $R^1$ is —C(O)NH(CH$_3$) or C(O)N(CH$_3$)$_2$.

In another embodiment, the Triazaspiro Compounds of formula (Ib) are those wherein $R^1$ is —CN.

In another embodiment, the Triazaspiro Compounds of formula (Ib) are those wherein $R^1$ is —N(H)S(O)$_2$(C$_1$–C$_4$ alkyl). In antoher embodiment, $R^1$ is N(H)S(O)$_2$(CH$_3$).

In another embodiment, the Triazaspiro Compounds of formula (Ib) are those wherein $R^1$ is

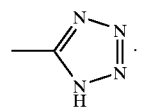

In another embodiment, the Triazaspiro Compounds of formula (Ib) are those wherein $R^2$ is —COOH or —COOR$^3$, and $R^3$ is —($C_1$–$C_6$ alkyl), benzyl, phenyl, or —($C_3$–$C_6$ cycloalkyl). In another embodiment, $R^3$ is —$CH_3$.

In another embodiment, the Triazaspiro Compounds of formula (Ib) are those wherein $R^2$ is —$C(O)N(CH_3)_2$.

In another embodiment, the Triazaspiro Compounds of formula (Ib) are those wherein $R^2$ is

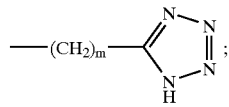

and m is an integer ranging from 0 to 4. In another embodiment, m is 0 or 1. In another embodiment, m is 0.

In another embodiment, the Triazaspiro Compounds of formula (Ib) are those wherein $R^1$ is —COOH and $R^2$ is —$C(O)N(CH_3)_2$.

In another embodiment, the Triazaspiro Compounds of formula (Ib) are those wherein $R^1$ is —$COOR^3$, $R^2$ is —$C(O)N(CH_3)_2$ and $R^3$ is —($C_1$–$C_6$ alkyl), benzyl, phenyl, or —($C_3$–$C_6$ cycloalkyl). In another embodiment, $R^3$ is —$CH_3$.

Illustrative Triazaspiro Compounds of formula (Ib) are:

Compound AP

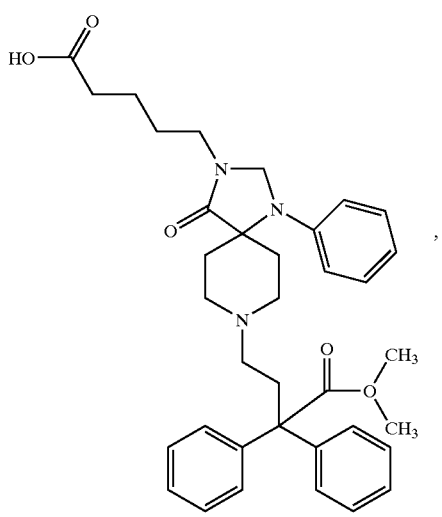

5-[8-(3-Dimethylcarbamoyl-3,3-diphenyl-propyl)-4-oxo-1-phenyl-1,3,8-triaza-spiro[4.5]dec-3-yl]-pentanoic acid;

Compound AQ

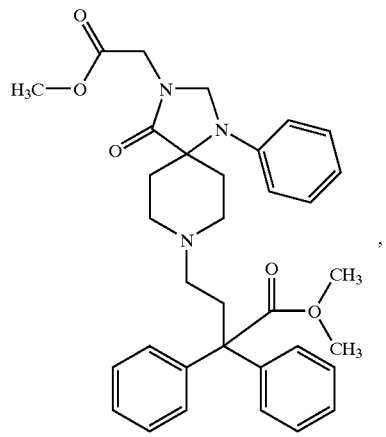

[8-(3-Dimethylcarbamoyl-3,3-diphenyl-propyl)-4-oxo-1-phenyl-1,3,8-triaza-spiro[4.5]dec-3-yl]-acetic acid methyl ester;

Compound AR

3-[8-(3-Dimethylcarbamoyl-3,3-diphenyl-propyl)-4-oxo-1-phenyl-1,3,8-triaza-spiro[4.5]dec-3-yl]-propionic acid ethyl ester;

Compound AT

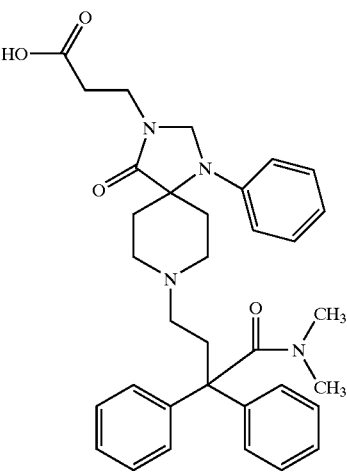

3-[8-(3-Dimethylcarbamoyl-3,3-diphenyl-propyl)-4-oxo-1-phenyl-1,3,8-triaza-spiro[4.5]dec-3-yl]-propionic acid; and pharmaceutically acceptable salts thereof.

4.2.3 The Triazaspiro Compounds of Formula (Ic)

The present invention also encompasses Triazaspiro Compounds having the formula (Ic):

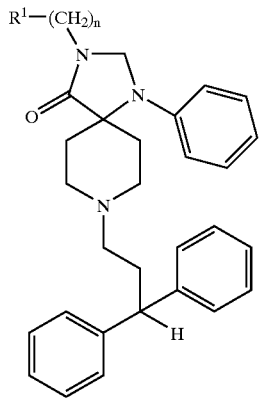

(Ic)

and pharmaceutically acceptable salts thereof, wherein:

$R^1$ is —COOH, —C(O)NH$_2$, —C(O)NH(C$_1$–C$_4$ alkyl), —C(O)N(C$_1$–C$_4$ alkyl)(C$_1$–C$_4$ alkyl), —N(H)S(O)$_2$(C$_1$–C$_4$ alkyl), or

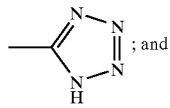 ; and n is an integer ranging from 1 to 4.

In one embodiment, the Triazaspiro Compounds of formula (Ic) are those wherein $R^1$ is —COOH.

In another embodiment, the Triazaspiro Compounds of formula (Ic) are those wherein $R^1$ is —C(O)NH$_2$, —C(O)NH(C$_1$–C$_4$ alkyl) or —C(O)N(C$_1$–C$_4$ alkyl)(C$_1$–C$_4$ alkyl). In another embodiment, $R^1$ is —C(O)NH(CH$_3$) or —C(O)N(CH$_3$)$_2$.

In another embodiment, the Triazaspiro Compounds of formula (Ic) are those wherein $R^1$ is —N(H)S(O)$_2$(C$_1$–C$_4$ alkyl). In another embodiment, $R^1$ is —NHS(O)$_2$(CH$_3$).

In another embodiment, the Triazaspiro Compounds of formula (Ic) are those wherein $R^1$ is

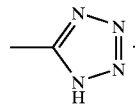.

In another embodiment, n is 0, 1, or 2. In another embodiment, n is 0 or 1. In another embodiment, n is 2.

Illustrative compounds of formula (Ic) are:

Compound AE

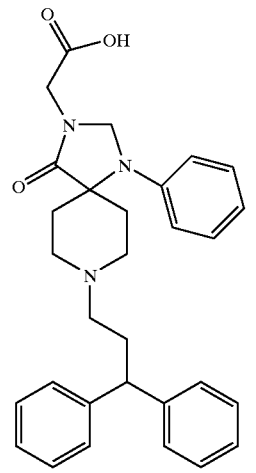

[8-(3,3-Diphenyl-propyl)-4-oxo-1-phenyl-1,3,8-triaza-spiro[4.5]dec-3-yl]-acetic acid;

Compound AL

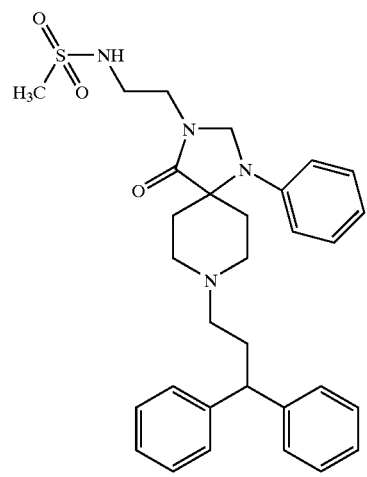

N-{2-[8-(3,3-Diphenyl-propyl)-4-oxo-1-phenyl-1,3,8-triaza-spiro[4.5]dec-3-yl]-ethyl}-methanesulfonamide;

Compound AM

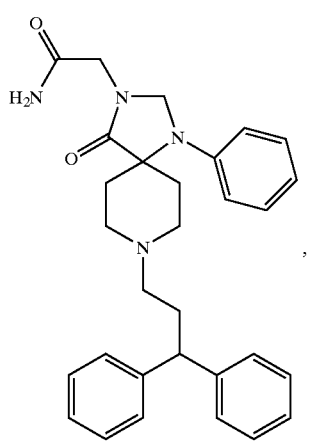

2-[8-(3,3-Diphenyl-propyl)-4-oxo-1-phenyl-1,3,8-triaza-spiro[4.5]dec-3-yl]-acetamide;

Compound AN

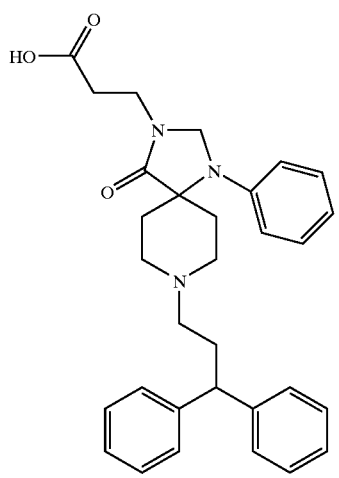

3-[8-(3,3-Diphenyl-propyl)-4-oxo-1-phenyl-1,3,8-triaza-spiro[4.5]dec-3-yl]-propionic acid;

Compound AO

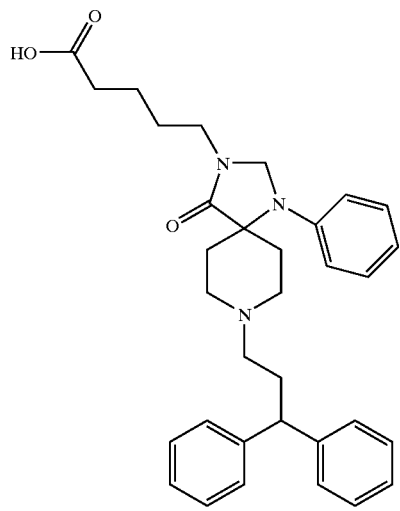

5-[8-(3,3-Diphenyl-propyl)-4-oxo-1-phenyl-1,3,8-triaza-spiro[4.5]dec-3-yl]-pentanoic acid;

Compound AW

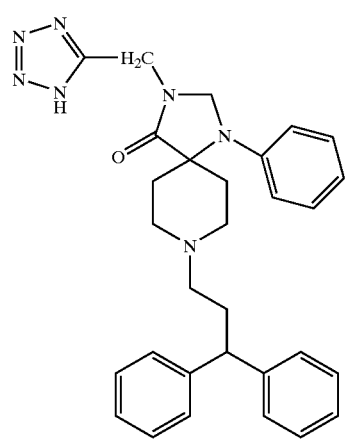

8-(3,3-diphenyl-propyl)-1-phenyl-3-(1H-tetrazol-5-ylmethyl)-1,3,8-triaza-spiro[4.5]decan-4-one;

Compound AX

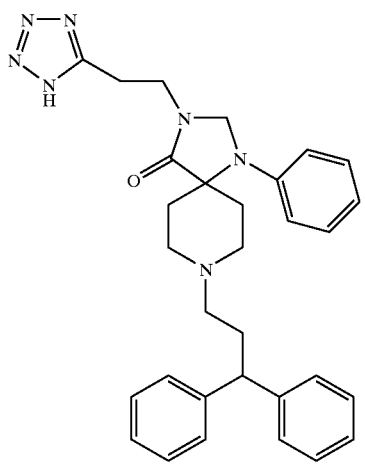

8-(3,3-Diphenyl-propyl)-1-phenyl-3-[2-(1H-tetrazol-5-yl)-ethyl]-1,3,8-triaza-spiro[4.5]decan-4-one;

and pharmaceutically acceptable salts thereof.

4.3 Other Triazaspiro Compounds

Other Triazaspiro Compounds are:

Compound AA

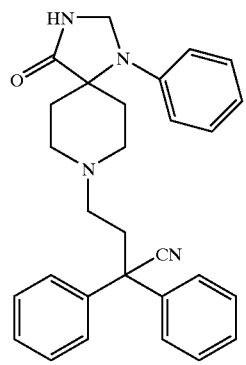

4-(4-Oxo-1-phenyl-1,3,8-triaza-spiro[4.5]dec-8-yl)-2,2-diphenyl-butyronitrile;

Compound AB

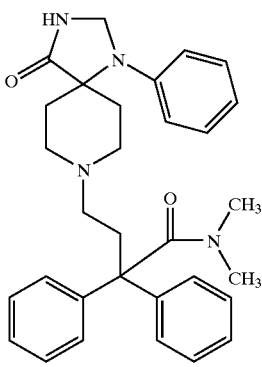

N,N-Dimethyl-4-(4-oxo-1-phenyl-1,3,8-triaza-spiro[4.5]dec-8-yl)-2,2-diphenyl-butyramide;

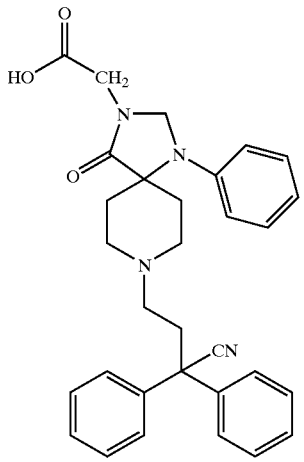

[8-(3-Cyano-3,3-diphenyl-propyl)-4-oxo-1-phenyl-1,3,8-triaza-spiro[4.5]dec-3-yl]-acetic acid;

Compound AD

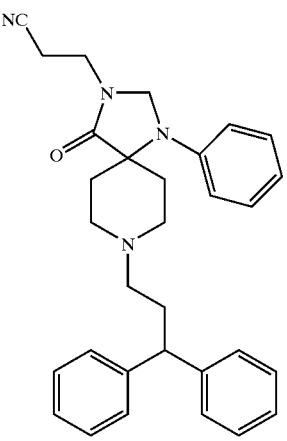

[8-(3-Cyano-3,3-diphenyl-propyl)-4-oxo-1-phenyl-1,3,8-triaza-spiro[4.5]dec-3-yl]-acetic acid ethyl ester;

Compound AI

3-[8-(3,3-Diphenyl-propyl)-4-oxo-1-phenyl-1,3,8-triaza-spiro[4.5]dec-3-yl]-propionitrile;

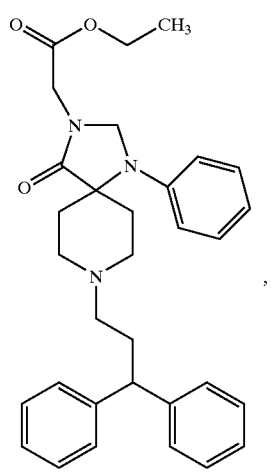

Compound AG

[8-(3,3-Diphenyl-propyl)-4-oxo-1-phenyl-1,3,8-triaza-spiro[4.5]dec-3-yl]-acetic acid ethyl ester;

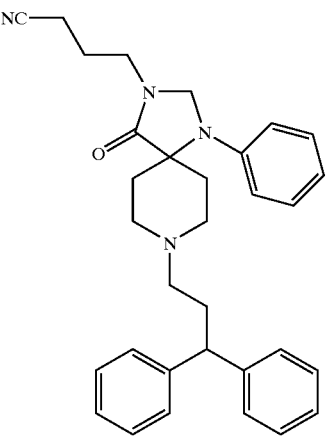

Compound AJ

4-[8-(3,3-Diphenyl-propyl)-4-oxo-1-phenyl-1,3,8-triaza-spiro[4.5]dec-3-yl]-butyronitrile;

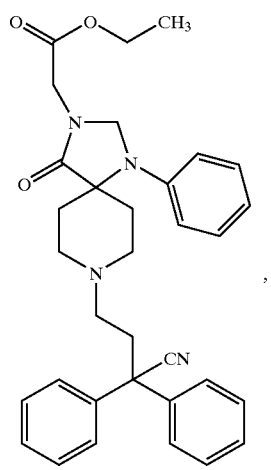

Compound AH

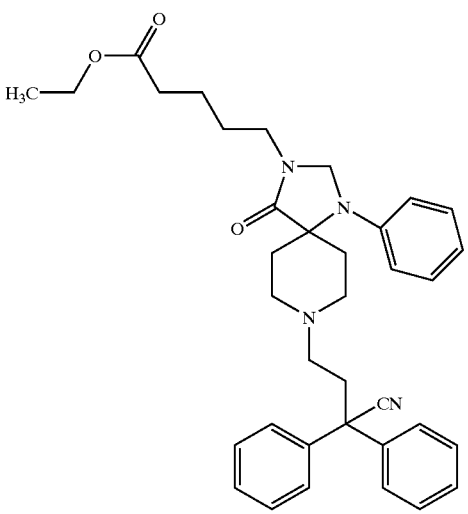

Compound AS

5-[8-(3-Cyano-3,3-diphenyl-propyl)-4-oxo-1-phenyl-1,3,8-triaza-spiro[4.5]dec-3-yl]-pentanoic acid ethyl ester;

Compound AU

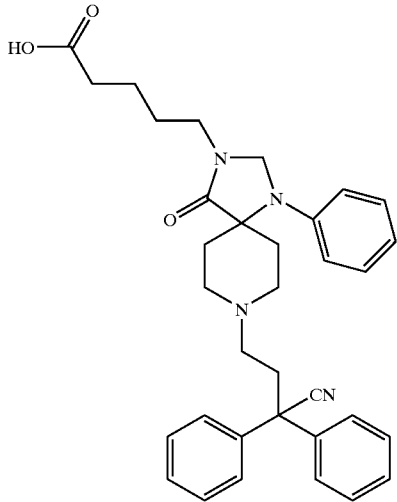

5-[8-(3-Cyano-3,3-diphenyl-propyl)-4-oxo-1-phenyl-1,3,8-triaza-spiro[4.5]dec-3-yl]-pentanoic acid;

Compound AV

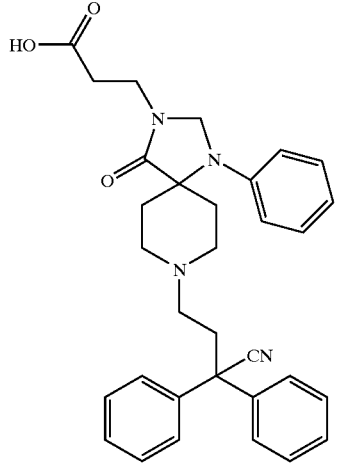

3-[8-(3-Cyano-3,3-diphenyl-propyl)-4-oxo-1-phenyl-1,3,8-triaza-spiro[4.5]dec-3-yl]-propionic acid;

Compound G

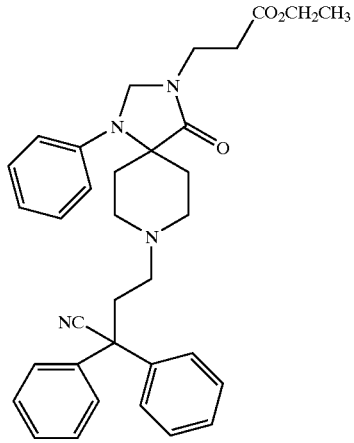

3-[8-(3-cyano-3,3-diphenyl-propyl)-4-oxo-1-phenyl-1,3,8-triaza-spiro[4.5]dec-3-yl]-propionic acid ethyl ester;

and pharmaceutically acceptable salts thereof.

4.4 Methods for Making the Triazaspiro Compounds

The Triazaspiro Compounds can be made using conventional organic syntheses and/or by the following illustrative methods:

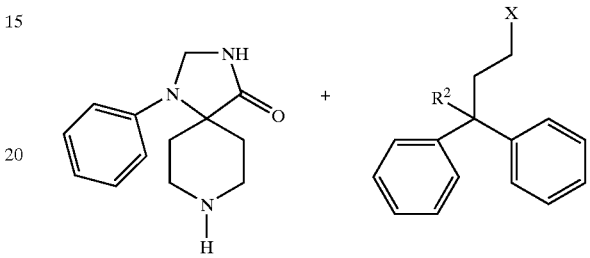

Compound A          Compound B

DIEA
acetonitrile,
heat

Compound C

The Triazaspiro Compounds wherein $R^1$ is H, n is 0, and $R^2$ is —$COOR^3$ (wherein $R^3$ is defined above) can be prepared by reacting Compound A with Compound B wherein $R^2$ is —$COOR^3$ (wherein $R^3$ is defined above) and X is a leaving group such as a benzenesulfonate, 4-methylbenzenesulfonate, 4-bromobenzenesulfonate, 4-nitrobenzenesulfonate, methanesulfonate, trifluoromethanesulfonate, or halogen in the presence of an organic base, such as pyridine, 4-dimethylpyridine, triethylamine, or diisopropylethylamine (DIEA), in an aprotic solvent to provide Compound C wherein $R^2$ is —$COOR^3$ (wherein $R^3$ is defined above). In one embodiment X is I or Br. Suitable aprotic solvents include, but are not limited to, acetonitrile, dimethylsulfoxide (DMSO), dimethylformamide (DMF), dichloromethane (DCM), 1,2-dichloroethane, tetrahydrofuran (THF), diethyl ether, ligroin, pentane, hexane, and dioxane. In one embodiment the aprotic solvent is acetonitrile.

The Triazaspiro Compounds wherein $R^1$ is H, n is 0, and $R^2$ is —COOH can be prepared by hydrolyzing Compound C wherein $R^2$ is —COOR$^3$ (wherein $R^3$ is defined above). The hydrolysis can be performed using an excess of an aqueous base, such as about 0.01 to about 1 N alkali metal hydroxide and then acidifying the hydrolysis product. The acidifying can be performed using about 0.01 to 3 N acid. In one embodiment the acid HCl. In one embodiment the alkali metal hydroxide is potassium hydroxide.

The Triazaspiro Compounds wherein $R^1$ is H, n is 0, and $R^2$ is

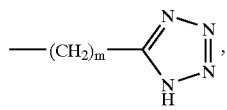

(wherein m is defined above) can be prepared by reacting Compound A and Compound B wherein $R^2$ is —(CH$_2$)$_m$CN to obtain Compound C wherein $R^2$ is —(CH$_2$)$_m$CN. Compound C wherein $R^2$ is —(CH$_2$)$_m$CN is then reacted with trimethylsilylazide ("TMSN$_3$-") in the presence of tin oxide according to the procedure described in S. J. Wittenberg et al., *J. Org. Chem.* 58;4139–4141 (1993).

The Triazaspiro Compound wherein $R^1$ is H, n is 0, and $R^2$ is —C(O)N(CH$_3$)$_2$ (Compound AB) can be prepared as described below:

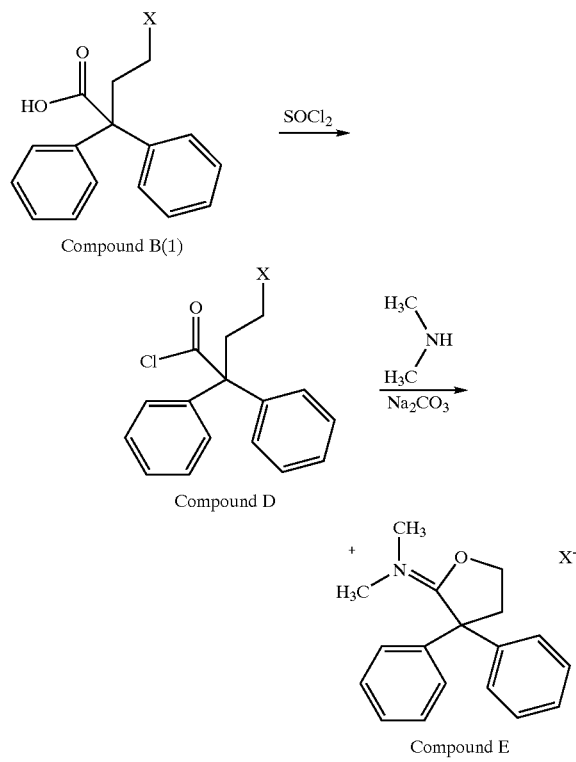

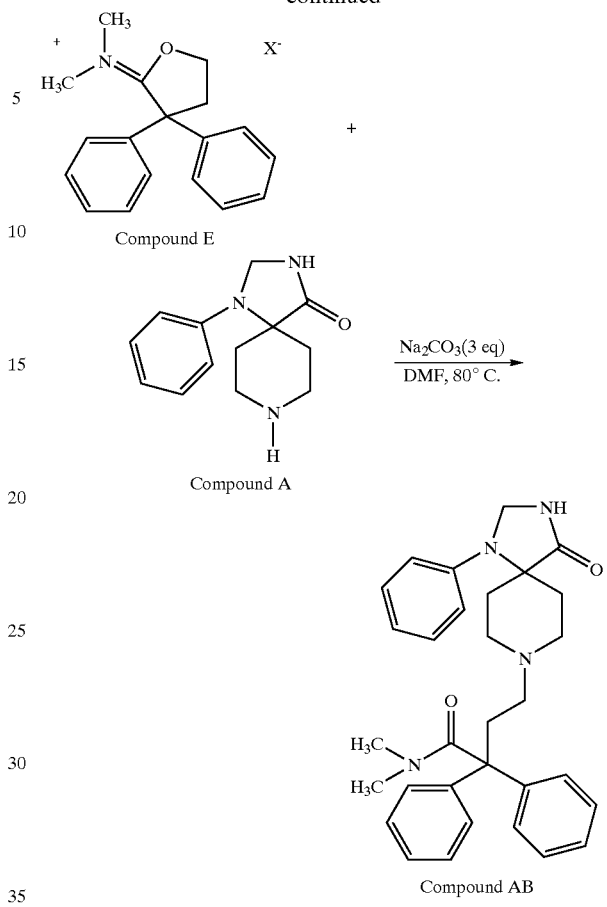

Compound B(1) (obtainable by hydrolyzing Compound B wherein $R^2$ is —COOR$^3$) is converted to an acid chloride using thionyl chloride or oxaloyl chloride to provide Compound D. Methods for obtaining acid chlorides are well known to those skilled in the art. Compound D is then reacted with about 1 to about 10 molar eq. of dimethylamine and an alkali metal carbonate, an alkali metal bicarbonate, or an alkaline earth carbonate to provide Compound E. One eq. of Compound E is then reacted with about 1 eq. of Compound A in the presence of an alkali metal carbonate, an alkali metal bicarbonate, or an alkaline earth carbonate in an aprotic solvent defined above to provide Compound AB. In one embodiment the alkali metal carbonate is Na$_2$CO$_3$. In another embodiment the aprotic solvent is DMF. Typically the reaction of Compound A and Compound E is conducted at a temperature of from about room temperature to about 100° C.

Compound C wherein $R^2$ is H can be prepared by reacting Compound A with Compound B wherein $R^2$ is H, and X is a leaving group such as a benzenesulfonate, 4-methylbenzenesulfonate, 4-bromobenzenesulfonate, 4-nitrobenzenesulfonate, methanesulfonate, trifluoromethanesulfonate, or halogen in the presence of an organic base, such as pyridine, 4-dimethylpyridine, triethylamine, or diisopropylethylamine (DIEA), in an aprotic solvent. In one embodiment X is I or Br. Suitable aprotic solvents include, but are not limited to, acetonitrile, dimethylsulfoxide (DMSO), dimethylformamide (DMF), dichloromethane (DCM), 1,2-dichloroethane, tetrahydrofuran (THF), diethyl ether, ligroin, pentane, hexane, and dioxane. In one embodiment the aprotic solvent is acetonitrile.

The Triazaspiro Compounds wherein $R^1$ is other than H and n is an integer ranging from 1 to 4 can be prepared by reacting Compound C wherein $R^2$ is H, —$COOR^3$, —C(O)N(CH$_3$)$_2$, or

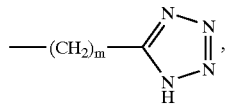

(wherein $R_3$ and m are defined above), with a compound of general formula $R^1(CH_2)_n$—X wherein $R^1$ is other than H and is defined above, n is an integer ranging from 1 to 4 and X is a leaving group such as a benzenesulfonate, 4-methylbenzenesulfonate, 4-bromobenzenesulfonate, 4-nitrobenzenesulfonate, methanesulfonate, trifluoromethanesulfonate, or halogen in the presence of a strong base such as lithium diisopropylamide or sodium hydride and an aprotic solvent such as THF, dioxane, or DMF. In one embodiment X is a halogen. In another embodiment X is I or Br. In another embodiment the base is NaH. In another embodiment the solvent is DMF.

The Triazaspiro Compounds wherein $R^1$ is other than H and $R^2$ is —COOH can be prepared by hydrolyzing the Triazaspiro Compounds wherein $R^1$ is other than H and $R^2$ is —$COOR^3$ (wherein $R^3$ is defined above). The hydrolysis can be performed using an excess of an aqueous base, such as about 0.01 to about 1 N alkali metal hydroxide and then acidifying the hydrolysis product. The acidifying can be performed using about 0.01 to 3 N acid. In one embodiment the acid HCl. In one embodiment the alkali metal hydroxide is potassium hydroxide.

Compound A is commercially available from Sigma-Aldrich, St. Louis, Mo. (www.sigma-aldrich.com).

Compound B wherein $R^2$ is —COOH and X is Br is commercially available from Sigma-Aldrich, St. Louis, Mo. (www.sigma-aldrich.com).

Compound B wherein $R^2$ is —$COOR^3$ is obtainable by esterifying Compound B wherein $R^2$ is —COOH (or a derivative thereof) and X is Br. Methods for esterifying carboxylic acids and derivatives thereof are well known to those skilled in the art (See, e.g., J. March, *Advanced Organic Chemistry, Reaction Mechanisms and Structure* 392–396 and 400 (4$^{th}$ ed. 1992)).

Compound B wherein $R^2$ is —CN and X is Br is commercially available from Sigma-Aldrich, St. Louis, Mo. (www.sigma-aldrich.com).

Compound B wherein $R^2$ is —$(CH_2)_mCN$, m is an integer ranging from 1 to 4 and X is Br is commercially available Sigma-Aldrich, St. Louis, Mo. (www.sigma-aldrich.com).

Compounds of general formula $R^1$ $(CH_2)_n$—X wherein $R^1$ is —COOH, X is a halogen, and n is an integer ranging from 1 to 4 are commercially available from Sigma-Aldrich, St. Louis, Mo. (www.sigma-aldrich.com).

Compounds of general formula $R^1(CH_2)_n$—X wherein $R^1$ is —$COOR^3$ (wherein $R_3$ is defined above), X is a halogen, and n is an integer ranging from 1 to 4 are obtainable by esterifying compounds of general formula $R^1(CH_2)_n$—X wherein $R^1$ is —COOH (or a derivative thereof). Methods for esterifying carboxylic acids or derivatives thereof are well known to those skilled in the art (See, e.g., J. March, *Advanced Organic Chemistry, Reaction Mechanisms and Structure* 392–396 and 400 (4$^{th}$ ed. 1992)).

Compounds of general formula $R^1(CH_2)_n$—X wherein $R^1$ is —$C(O)NH_2$, —$C(O)NH(C_1-C_4$ alkyl) or —$C(O)N(C_1-C_4$ alkyl)$(C_1-C_4$ alkyl); X is a halogen; and n is an integer ranging from 1 to 4 are obtainable by aminating a compound of general formula $R^1(CH_2)_n$—X wherein $R^1$ is —COOH (or a derivative thereof). Methods for aminating carboxylic acids or derivatives thereof are well known to those skilled in the art (See, e.g., J. March, *Advanced Organic Chemistry, Reaction Mechanisms and Structure* 417–424 (4$^{th}$ ed. 1992)).

Compounds of general formula $R^1(CH_2)_n$—X wherein $R^1$ is —$N(H)S(O)_2(C_1-C_4$ alkyl), X is a halogen, and n is an integer ranging from 1 to 4 can be obtained by reacting an amine of formula $NH_2$—$(CH_2)_n$—X, wherein X is a halogen, and n is an integer ranging from 1 to 4 (commercially available from Sigma-Aldrich, St. Louis, Mo. (www.sigma-aldrich.com) with a sulfonyl chloride of formula Cl—$S(O)_2(C_1-C_4$ alkyl). The sulfonyl halides are commercially available or can be made by methods well known to those skilled in the art (See, e.g., J. March, *Advanced Organic Chemistry, Reaction Mechanisms and Structure*, 499 (4$^{th}$ ed. 1992)).

Compounds of general formula $R^1(CH_2)_n$—X wherein $R^1$ is —CN, X is a halogen, and n is an integer ranging from 1 to 4 are commercially available from Sigma-Aldrich, St. Louis, Mo. (www.sigma-aldrich.com).

Compounds of general formula $R^1$ $(CH_2)_n$—X wherein $R^1$ is

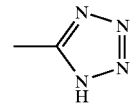

are obtainable by reacting compounds of general formula R $(CH_2)_n$—X wherein $R^1$ is —CN, X is a halogen, and n is an integer ranging from 1 to 4 with TMSN$_3$ in the presence of tin oxide as described in S. J. Wittenberg et al., *J. Org. Chem.* 58:4139–4141 (1993).

Certain Triazaspiro Compounds can have asymmetric centers and therefore exist in different enantiomeric and diastereomeric forms. A Triazaspiro Compound can be in the form of an optical isomer or a diastereomer. Accordingly, the invention encompasses Triazaspiro Compounds and their uses as described herein in the form of their optical isomers, diastериomers, and mixtures thereof, including a racemic mixture.

In addition, one or more hydrogen, carbon or other atoms of a Triazaspiro Compound can be replaced by an isotope of the hydrogen, carbon or other atoms. Such compounds, which are encompassed by the present invention, are useful as research and diagnostic tools in metabolism pharmacokinetic studies and in binding assays.

4.5 Therapeutic Uses of the Triazaspiro Compounds

In accordance with the invention, the Triazaspiro Compounds are administered in certain embodiments, to an animal, e.g. a mammal or a human, for the treatment or prevention of pain. The Triazaspiro Compounds can be used to treat or prevent acute or chronic pain. For example, the Triazaspiro Compounds can be used for, but are not limited to, treating or preventing cancer pain, central pain, labor pain, myocardial infarction pain, pancreatic pain, colic pain, post-operative pain, headache pain, muscle pain, and pain associated with intensive care.

The Triazaspiro Compounds can also be used for inhibiting, preventing, or treating pain associated with inflammation or with an inflammatory disease in an animal. The pain to be inhibited, treated or prevented may be associated with inflammation associated with an inflammatory disease, which can arise where there is an inflammation of the body tissue, and which can be a local inflammatory response and/or a systemic inflammation. For example, the Triazaspiro Compounds can be used to inhibit, treat, or prevent pain associated with inflammatory diseases including, but not limited to: organ transplant rejection; reoxygenation injury resulting from organ transplantation (see Grupp et al,. *J. Mol. Cell Cardiol.* 31:297–303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyclinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Triazaspiro Compounds can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Without wishing to be bound by theory, it is believed that the Triazaspiro Compounds are agonists for an opioid receptor.

The invention also relates to methods for stimulating opioid-receptor function in a cell comprising contacting a cell capable of expressing an opioid receptor with an effective amount of a Triazaspiro Compound. The method is also useful for stimulating opioid receptor function in a cell in vivo, in an animal, such as a human, by contacting a cell capable of expressing an opioid receptor, in an animal, with an effective amount of a Triazaspiro Compound. In one embodiment, the method is useful for treating or preventing pain in an animal. Brain tissue, spinal chord tissue, immune cells, cells of the gastrointestinal tract, and primary afferent nerve cells are examples of tissues and/or cells that can express an opioid receptor. This method can be used in vitro, for example, as an assay to select cells that express an opioid receptor.

4.5.1 Therapeutic/Prophylactic Administration and Compositions of the Invention

Due to their activity, the Triazaspiro Compounds are advantageously useful in veterinary and human medicine. As described above, the Triazaspiro Compounds are useful for treating or preventing pain in an animal in need thereof.

When administered to an animal, the Triazaspiro Compounds can be administered as a component of a composition that comprises a pharmaceutically acceptable carrier or excipient. The present compositions, which comprise a Triazaspiro Compound, are, in certain embodiments, administered orally. The compositions of the invention can also be administered by any other convenient route, for example, by infusion or bolus injection, by absorption through epithelial or mucocutaneous linings (e.g., oral mucosa, rectal, and intestinal mucosa, etc.) and can be administered together with another therapeutic agent. Administration can be systemic or local. Various delivery systems are known, e.g., encapsulation in liposomes, microparticles, microcapsules, capsules, etc., and can be used to administer the Triazaspiro Compounds.

Methods of administration include but are not limited to intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Triazaspiro Compounds into the bloodstream.

In specific embodiments, the Triazaspiro Compounds can be administered locally. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Triazaspiro Compounds can be formulated as a suppository, with traditional binders and excipients such as triglycerides.

In another embodiment, the Triazaspiro Compounds can be delivered in a vesicle, in particular a liposome (see Langer, *Science* 249:1527–1533 (1990) and Treat et al., *Liposomes in the Therapy of Infectious Disease and Cancer* 317–327 and 353–365 (1989).

In yet another embodiment, the Triazaspiro Compounds can be delivered in a controlled-release system (see, e.g., Goodson, in Medical Applications of Controlled Release, supra, vol. 2, pp. 115–138 (1984)). Other controlled-release systems discussed in the review by Langer, *Science* 249:1527–1533 (1990) may be used. In one embodiment, a pump may be used (Langer, *Science* 249:1527–1533 (1990); Sefton, *CRC Crit. Ref. Biomed. Eng.* 14:201 (1987); Buchwald et al., *Surgery* 88:507 (1980); and Saudek et al., *N.*

Engl. J. Med. 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled-release system can be placed in proximity of a target of the Triazaspiro Compound thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea, and the like. In addition, auxiliary, stabilizing, thickening, lubricating, and coloring agents may be used. When administered to an animal, the pharmaceutically acceptable excipients are, in certain embodiments, sterile. Water is a particularly useful excipient when the Triazaspiro Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

Suitable pharmaceutically acceptable carriers or excipients for intravenous administration of the Triazaspiro Compounds include, but are not limited to, normal (about 0.9%) saline, about 25 to about 30% polyethylene glycol ("PEG") diluted with saline or water, and about 2 to about 30% hydroxy propyl β-cyclodextrin diluted with water.

Suitable pharmaceutically acceptable carriers or excipients for intraperitoneal administration of the Triazaspiro Compounds include, but are not limited to, normal (about 0.9%) saline, about 25 to about 30% polyethylene glycol ("PEG") diluted with saline or water, about 25 to about 30% propylene glycol (PG) diluted with saline or water, and about 2 to about 30% hydroxypropyl β-cyclodextrin diluted with water.

Suitable pharmaceutically acceptable carriers or excipients for subcutaneous and intramuscular administration of the Triazaspiro Compounds include, but are not limited to, normal (about 0.9%) saline, about 25 to about 30% polyethylene glycol ("PEG") diluted with saline or water, about 25 to about 30% propylene glycol (PG) diluted with saline or water, and water.

Suitable pharmnaceutically acceptable carriers or excipients for oral administration of the Triazaspiro Compounds include, but are not limited to, normal (about 0.9%) saline, about 25 to about 30% polyethylene glycol ("PEG") diluted with saline or water, about 2 to about 30% hydroxypropyl β-cyclodextrin diluted with water, about 25 to about 30% propylene glycol (PG) diluted with saline or water, about 1 to about 5% methylcellulose diluted with water, and water.

Suitable pharmaceutically acceptable carriers or excipients for intracerebroventricular and intrathecal administration of the Triazaspiro Compounds include, but are not limited to, normal (about 0.9%) saline.

The present compositions can take the form of solutions, suspensions, emulsion, tablets, pills, pellets, capsules, capsules containing liquids, powders, sustained-release formulations, suppositories, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447–1676 (Alfonso R. Gennaro ed., 19th ed. 1995), incorporated herein by reference.

In one embodiment, the Triazaspiro Compounds are formulated in accordance with routine procedures as a composition adapted for oral administration to an animal, particularly a human being. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate-release formulations. A time delay material such as glycerol monostearate or glycerol stearate can also be used. Oral compositions can include standard excipients such as mannitol, lactose, starch, magnesium stearate, sodium saccharin, cellulose and magnesium carbonate. Such excipients are, in certain embodiments, of pharmaceutical grade.

In another embodiment, the Triazaspiro Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen any pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the Triazaspiro Compounds are to be administered by infusion, they can be dispensed, for example, from an infusion bottle containing sterile pharmaceutical grade water or saline. Where the Triazaspiro Compounds are administered by injection, an ampoule of sterile water for injection or saline can be provided so that the ingredients can be mixed prior to administration.

The Triazaspiro Compounds can be administered by controlled-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical compositions can have a common goal of improving drug therapy over that achieved by their non-controlled counterparts. In one embodiment a controlled-release composition comprises a minimal amount of a Triazaspiro Compound to cure or control the condition in a minimum amount of time. Advantages of controlled-release compositions include extended activity of the drug, reduced dosage frequency, and increased patient compliance. In addition, controlled-release compositions can favorably affect the time of onset of action or other characteristics, such as blood levels of the Triazaspiro Compound, and can thus reduce the occurrence of side (e.g., adverse) effects.

Controlled-release compositions can initially release an amount of a Triazaspiro Compound that promptly produces the desired therapeutic effect, and gradually and continually release other amounts of the Triazaspiro Compound to maintain this level of therapeutic or prophylactic effect over an extended period of time. To maintain this constant level of the Triazaspiro Compound in the body, the Triazaspiro Compound can be released from the dosage form at a rate that will replace the amount of Triazaspiro Compound being metabolized and excreted from the body. Controlled-release of an active ingredient can be stimulated by various conditions including, but not limited to, changes in pH, changes in temperature, concentration or availability of enzymes, concentration or availability of water, or other physiological conditions or compounds.

The amount of the Triazaspiro Compound that is effective in the treatment or prevention of pain depends on the nature of the disorder or condition causing the pain and can be determined by standard clinical techniques. In addition, in vitro or in vivo assays can optionally be employed to help identify optimal dosage ranges. The precise dose to be employed can also depend on the route of administration, and the seriousness of the pain and should be decided according to the judgment of the practitioner and each patient's circumstances in view of published clinical studies. Suitable effective amounts, however, range, in certain embodiments, from about 10 micrograms to about 2500 milligrams about every 4 h, although typically about 100 mg or less. In certain embodiments, the effective amount ranges from about 0.01 milligrams to about 100 milligrams of a Triazaspiro Compound about every 4 h, from about 0.020 milligrams to about 50 milligrams about every 4 h, and from about 0.025 milligrams to about 20 milligrams about every 4 h. The effective amounts described herein refer to total amounts administered; that is, if more than one Triazaspiro Compound is administered, the dosages correspond to the total amount administered.

Where a cell capable of expressing an opioid receptor is contacted with a Triazaspiro Compound in vitro, the effective amount will typically range, in certain embodiments, from about 0.01 mg to about 100 mg/L, from about 0.1 mg to about 50 mg/L, and from about 1 mg to about 20 mg/L, of a solution or suspension of a pharmaceutically acceptable carrier or excipient.

Where a cell capable of expressing an opioid receptor is contacted with a Triazaspiro Compound in vivo, the effective amount will typically range, in certain embodiments, from about 0.01 mg to about 100 mg/kg of body weight per day, from about 0.1 mg to about 50 mg/kg body weight per day, and from about 1 mg to about 20 mg/kg of body weight per day.

The Triazaspiro Compounds are, in certain embodiments, assayed in vitro or in vivo for the desired therapeutic or prophylactic activity prior to use in humans. Animal model systems can be used to demonstrate safety and efficacy.

The present methods for treating or preventing pain in an animal can further comprise administering to the animal being administered a Triazaspiro Compound an effective amount of another therapeutic agent.

The present methods for stimulating opioid-receptor function in a cell can further comprise contacting the cell with an effective amount of another therapeutic agent.

Examples of other therapeutic agents include, but are not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a Ca2+-channel blocker, an anticancer agent, an anti-anxiety agent, an agent for treating or preventing an addictive disorder and mixtures thereof.

Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the Triazaspiro Compound is less than its effective amount would be where the other therapeutic agent is not administered. In this case, without being bound by theory, it is believed that the Triazaspiro Compound and the other therapeutic agent act synergistically to treat or prevent pain.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non-limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Antiinflammatory Agents and Drugs Employed in the Treatment of Gout, in Goodman & Gilman's The Pharmacological Basis of Therapeutics* 617–57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy Vol II* 1196–1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Cox-II inhibitors include, but are not limited to, rofecoxib and celecoxib.

Examples of useful antimigraine agents include, but are not limited to, alpipride, dihydroergotamine, dolasetron, ergocomine, ergocominine, ergocryptine, ergot, ergotamine, flumedroxone acetate, fonazine, lisuride, lomerizine, methysergide oxetorone, pizotyline, and mixtures thereof.

The other therapeutic agent can also be an agent useful for reduce any potential side effects of a Triazaspiro Compound. For example, the other therapeutic agent can be an antiemetic agent. Useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dotbiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflomithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormnaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other useful anti-cancer agents include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytok ine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful anti-anxiety agents include, but are not limited to, benzodiazepines, such as alprazolam, chlordiazepoxide, clonazepam, clorazepate, diazepam, halazepam, lorazepam, oxazepam, and prazepam; non-benzodiazepine agents, such as buspirone; and tranquilizers, such as barbituates.

A Triazaspiro Compound and the other therapeutic agent can act additively or, in one embodiment, synergistically. In one embodiment, a Triazaspiro Compound is administered concurrently with another therapeutic agent. In one embodiment, a composition comprising an effective amount of a Triazaspiro Compound and an effective amount of another therapeutic agent can be administered. Alternatively, a composition comprising an effective amount of a Triazaspiro Compound and a different composition comprising an effective amount of another therapeutic agent can be concurrently administered. In another embodiment, an effective amount of a Triazaspiro Compound is administered prior or subsequent to administration of an effective amount of another therapeutic agent. In this embodiment, the Triazaspiro Compound is administered while the other therapeutic agent exerts its therapeutic effect, or the other thereapeutic agent is administered while the Triazaspiro Compound exerts its preventive or therapeutic effect for treating or preventing pain.

In another embodiment, a composition of the invention is prepared by a method comprising admixing a Triazaspiro Compound or pharmaceutically acceptable salt and a pharmaceutically acceptable carrier or excipient. Admixing can be accomplished using methods well known for admixing a compound (or salt) and a pharmaceutically acceptable carrier or excipient. In one embodiment, the Triazaspiro Compound or the pharmaceutically acceptable salt of the Compound is present in the composition in an effective amount.

4.5.2 Kits

The invention encompasses kits that can simplify the administration of a Triazaspiro Compound to an animal.

A typical kit of the invention comprises a unit dosage form of a Triazaspiro Compound. In one embodiment, the unit dosage form is a container, which in certain embodiments, is a sterile container, containing an effective amount of a Triazaspiro Compound and a pharmaceutically acceptable carrier or excipient. The kit can further comprise a label or printed instructions instructing the use of the Triazaspiro Compound to treat or prevent pain. The kit can also further comprise a unit dosage form of another therapeutic agent, for example, a container containing an effective amount of the other therapeutic agent. In one embodiment, the kit comprises a container containing an effective amount of a Triazaspiro Compound and an effective amount of another therapeutic agent. Examples of other therapeutic agents include, but are not limited to, those listed above.

Kits of the invention can further comprise a device that is useful for administering the unit dosage forms. Examples of such devices include, but are not limited to, syringes, drip bags, patches, and inhalers.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Examples 1–21 relate to the synthesis of illustrative Triazaspiro Compounds.

5.1 Example 1

Synthesis of Compound AC

5.2 Example 2

Synthesis of Compound AF

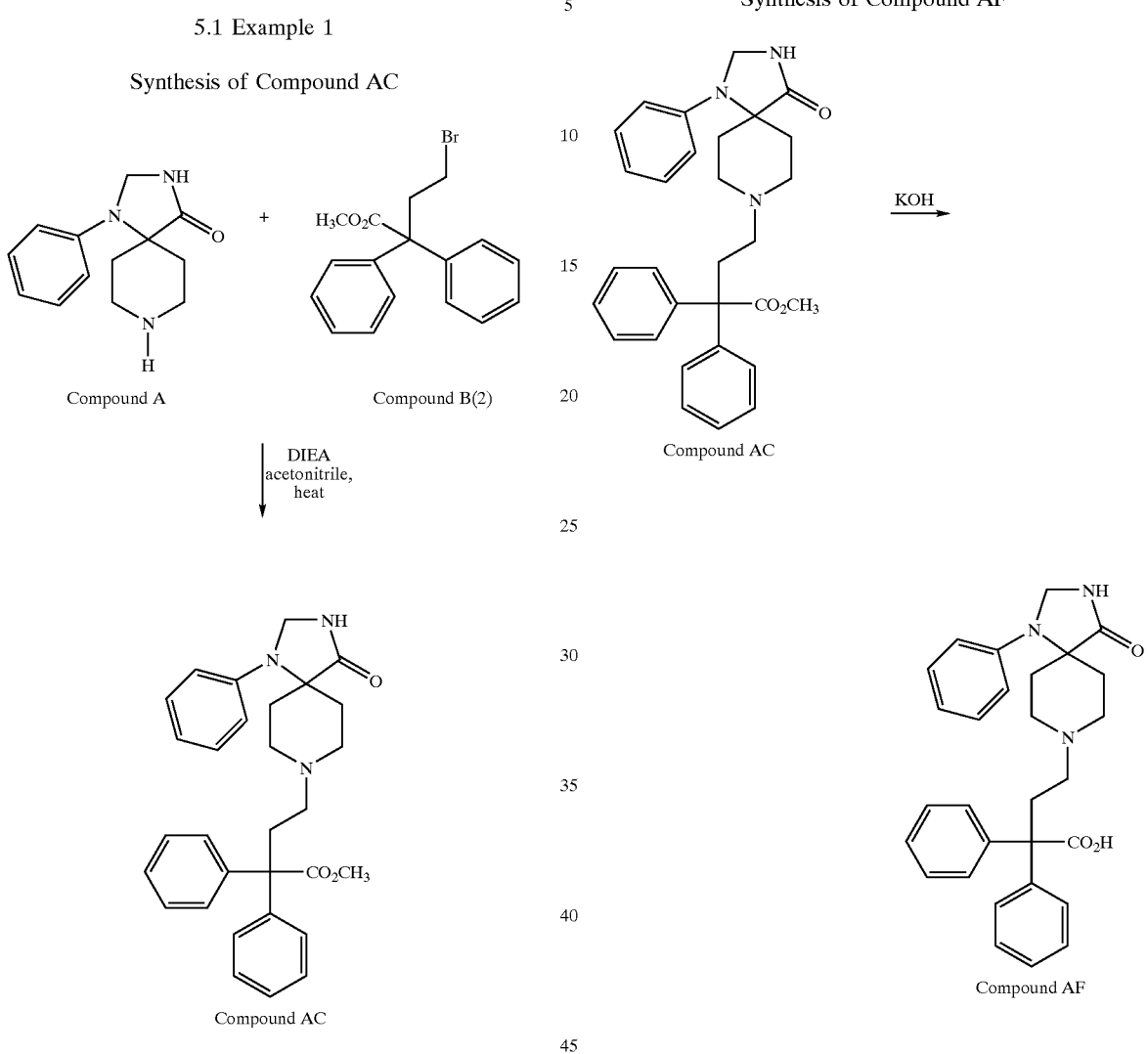

To a mixture of Compound A (2 mmol) and Compound B (2 mmol) in 6 mL of acetonitrile was added 1.5 eq. of diisopropylethylamine and the resulting mixture was heated to 60° C. and allowed to stir for about 12 h. Thin layer chromatography indicated the complete disappearance of Compound A. The solvent was removed under reduced pressure. The resulting residue was dissolved in 10 mL of ethyl acetate, washed with water (10 mL, 2 times), the organic layer dried ($K_2CO_3$), and the solvent removed under reduced pressure. The resulting residue was purified by column chromatography using a silica column eluted with 5% triethylamine, 25% ethyl acetate, and 70% hexane to provide 120 mg of Compound AC (yield 10.6%). Compound AC was shown to be greater than 97% pure by high pressure liquid chromatography (HPLC) analysis.

The identity of Compound AC was confirmed using $^1$H NMR and mass spectral (MS) analysis.

$^1$H NMR (CDCl$_3$): δ 1.6 (m, 2H), 2.2 (m, 2H), 2.55–2.8 (m, 8H), 3.7 (s, 3H), 4.75 (s, 2H), 6.5 (bs, 1H), 6.9 (m, 3H), 7.2–7.4 (m, 11H). MS: m/z 484.2.

Compound AF was prepared by dissolving Compound AC (0.5 mmol) in 3 mL of methanol and 40 mL of 40% aqueous potassium hydroxide and heating the resulting mixture at 80° C. with stirring for about 2 h. LC/MS indicated disappearance of Compound AC. Then 2 mL of water and 2 mL of 3N HCl was added to the mixture to adjust the pH to a value of about 1. The resulting precipitate was collected and dried under vacuum to provide 110 mg of Compound AF. Compound AF was shown to be greater than 97% pure by HPLC analysis.

The identity of compound AF was confirmed using $^1$H NMR and MS analysis.

$^1$H NMR (CD$_3$OD): δ 2.0 (d, 2H), 2.65–2.75 (m, 2H), 2.8–3.0 (m, 4H), 3.5 (m, 2H), 2.7 (m, 2H), 4.7 (s, 2H), 6.9–7.05 (m, 2H), 7.2–7.4 (m, 13H). MS: m/z 470.2.

5.3 Example 3

Synthesis of Compound AA

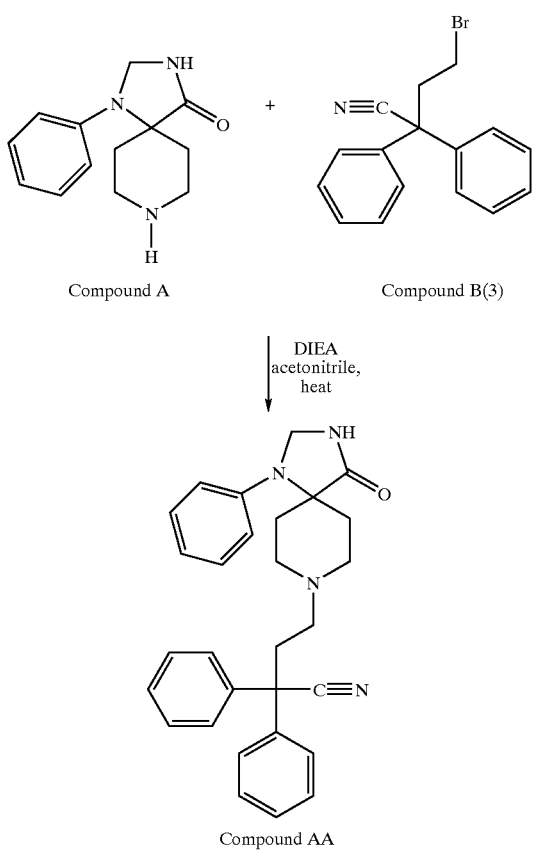

5.4 Example 4

Synthesis of Compound AK

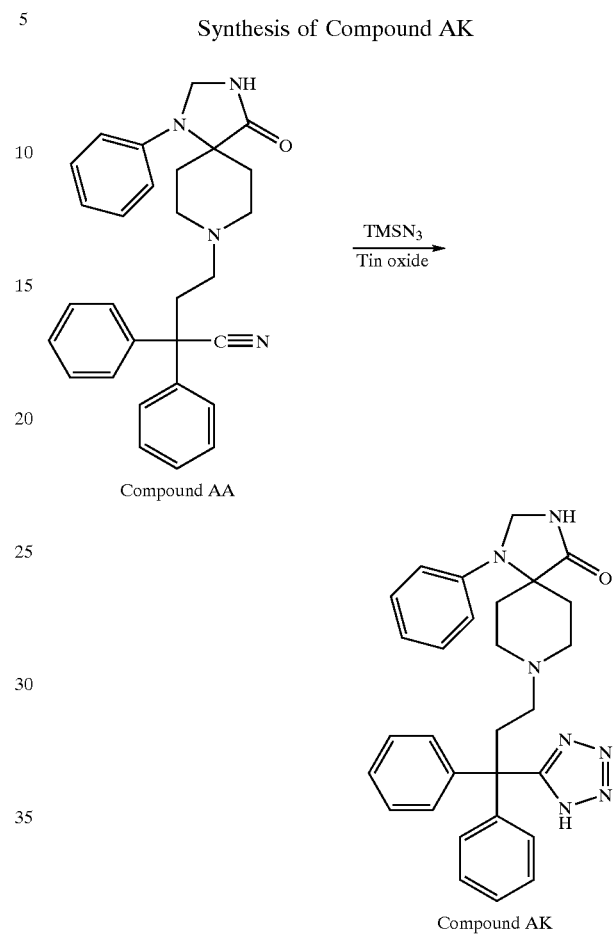

To a mixture of Compound A (3.6 mmol) (commercially available from Sigma-Aldrich, St. Louis, Mo., www.sigma-aldrich.com) and Compound B(3) (3.6 mmole) (commercially available from Sigma-Aldrich, St. Louis, Mo., www.sigma-aldrich.com) in 50 mL of acetonitrile was added in one portion 1.2 molar eq. of diisopropylethyamine (DIEA) and 3 drops of dimethylformamide (DMF). The resulting mixture was heated to 60° C. and allowed to stir for about 12 h. Thin-layer chromatography (TLC) indicated the disappearance of Compound A. The solvent was removed under reduced pressure and 50 mL of 1N NaOH and 50 mL of ethyl acetate were added to the resulting residue. The organic layer was separated and the aqueous layer washed with ethyl acetate (50 mL, 2 times). The organic layers were combined, dried ($K_2CO_3$), and the solvent removed under reduced pressure to provide a yellow oil that was purified using a silica gel column chromatography eluted with 5% triethylamine, 25% ethyl acetate, and 70% hexane. The relevant fractions were combined and concentrated to provide Compound AA. Compound AA was shown to be greater than 97% pure by HPLC analysis.

The identity of Compound AA was confirmed using $^1$H NMR and MS analysis.

$^1$H NMR (CDCl$_3$): δ 1.7 (d, 2H), 2.55 (dm, 2H), 2.65 (m, 4H), 2.7–2.9 (m, 4H), 3.7 (s, 2H), 6.25 (bs, 1H), 6.8–6.95 (m, 3H), 7.3–7.5 (m, 12H). MS: m/z 451.2.

To a solution of Compound AA (0.5 mmol) and trimethylsilylazide (1 mmol, 2 eq.) in 3 mL of toluene was added dibutyl tin oxide (0.1 eq.) and the resulting mixture was heated at 110° C. for about 24 h. LC/MS indicated compete disappearance of Compound AA. The solvent was removed under reduced pressure. The resulting residue was dissolved in CHCl$_3$ and purified using column chromatography on a florisil column eluted with 2% NH$_4$OH, 15% methanol, and 85% methylene chloride to provide 6 mg of Compound AK as a pale yellow solid. Compound AK was shown to be greater than 97% pure by HPLC analysis.

The identity of compound AK was confirmed using $^1$H NMR and MS analysis.

$^1$H NMR (CD$_3$OD): δ 2.0 (d, 2H), 2.9–3.0 (m, 4H), 3.1 (m, 2H), 3.4–3.5 (m, 2H), 3.6–3.7 (m, 2H), 4.75 (s, 2H), 6.9 (t, 1H), 7.0–7.1 (m, 5H), 7.2–7.3 (m, 5H), 7.35 (t, 2H), 7.8 (s, 2H). MS: m/z 494.

5.5 Example 5

Synthesis of Compound AB

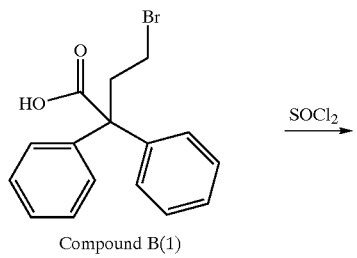

Compound B(1)

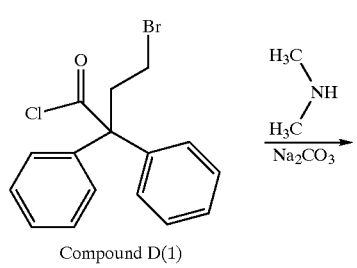

Compound D(1)

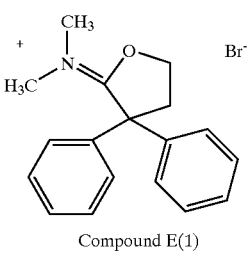

Compound E(1)

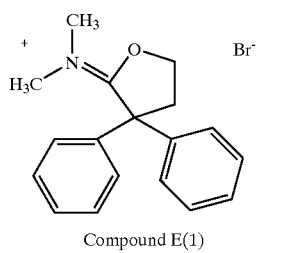

Compound E(1)

+

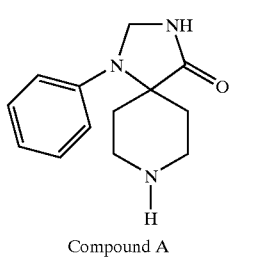

Compound A

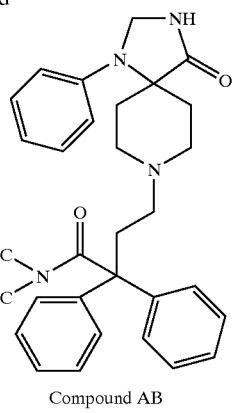

Compound AB

4-Bromo-2,2-diphenylbutyric acid (Compound B(1), 23 g, 72 mmol) was suspended in 150 mL of chloroform, and 20 mL of thionyl chloride (270 mmol) was added dropwise. After addition of the thionyl chloride, 0.2 mL of dimethylformamide was added and the resulting solution heated at reflux for about 4 h. The reaction mixture was then concentrated under reduced pressure to provide 4-bromo-2,2-diphenylbutyric chloride (Compound D(1)) as a pale yellow oil that was used in the following step without further purification.

To 100 mL of saturated aqueous $Na_2CO_3$ was added 50 mL of a 2M solution of dimethylamine in tetrahydrofuran. The resulting solution was cooled to 0° C. and a solution of Compound D(1), prepared as described above, dissolved in 100 mL of toluene was added dropwise. The resulting mixture was allowed to stir for about 12 h. The organic and aqueous layers of the reaction mixture were separated and the aqueous layer was extracted with 30 mL of toluene and then extracted 3 times with 100 mL of chloroform and the organic extracts were combined. The combined organic extracts were washed with water (30 mL), dried ($K_2CO_3$), and the solvent was removed under reduced pressure to provide a residue that was crystallized from methyl isobutyl ketone to provide 12 g (53% yield) of dimethyl(tetrahydro-3,3-diphenyl-2-furylidene)ammonium bromide (Compound E(1)).

To a mixture of Compound A (1 mmol) and Compound E(1) (1 mmol) in 4 mL of dimethylformamide was added 3 eq. of $Na_2CO_3$. The resulting mixture was heated at 80° C. with stirring for about 1.5 h. Thin layer chromatography showed the disappearance of Compound A. The solvent was removed under reduced pressure and 5 mL of 1 N NaOH and 10 mL of ethyl acetate were added to the residue. The organic layer was separated and the aqueous layer was washed with ethyl acetate (5 mL, 2 time). The organic layers were combined, dried ($K_2CO_3$), and the solvent removed under reduced pressure to provide a yellow oil that was purified by column chromatography using a silica column eluted with 5% triethylamine, 25% ethyl acetate, and 70% hexane to provide 284 mg of Compound AB as a solid (58% yield); Compound AB was shown to be greater than 97% pure by HPLC analysis.

The identity of compound AB was confirmed using $^1H$ NMR and MS analysis.

$^1H$ NMR (CDCl$_3$): δ 1.6 (d, 2H), 2.2 (m, 2H), 2.35 (m, 2H), 2.45–2.6 (m, 5H), 2.7 (m, 4H), 3.0 (m, 3H), 4.7 (s, 2H), 6.2 (bs, 1H), 6.8–6.9 (m, 3H), 7.3 (m, 4H), 7.35–7.5 (m, 8H). MS: m/z 497.2.

5.6 Example 6

Synthesis of Compound AR

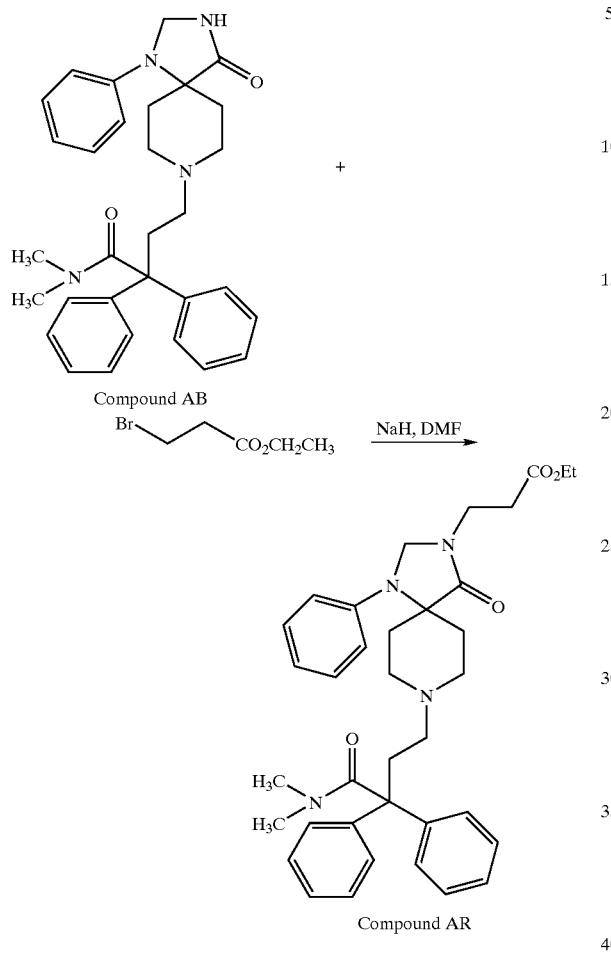

5.7 Example 7

Synthesis of Compound AT

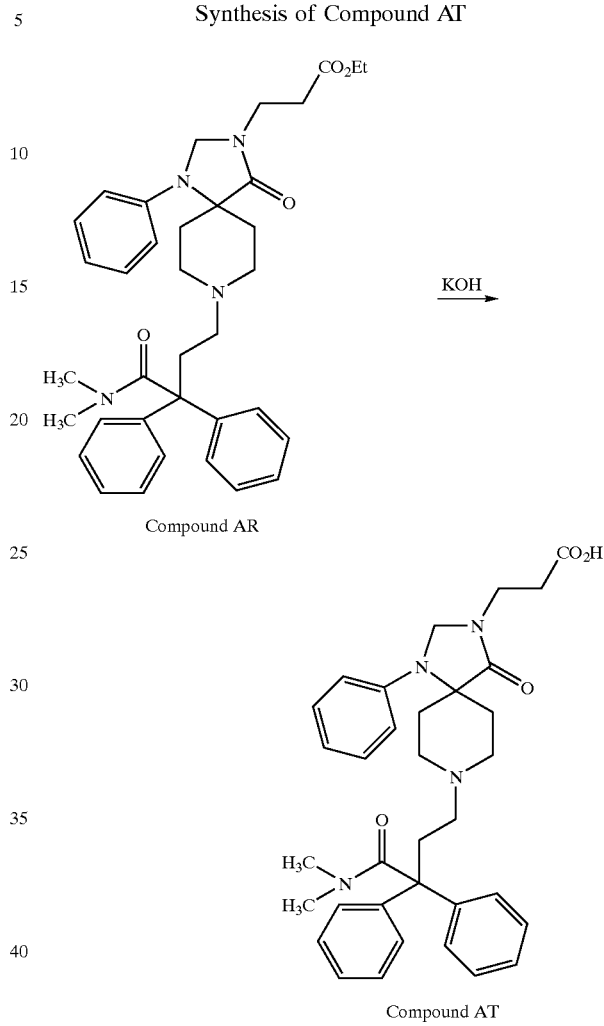

To 480 mg of Compound AB (1 mmol) in 5 mL of dimethylformamide was added abut 1.2 eq. of NaH that had been washed twice with tetrahydrofuran. Gas evolution occurred and, after 2 min., 1.1 eq. of ethylbromopropionate (commercially available from Sigma-Aldrich, St. Louis, Mo., www.sigma-aldrich.com) was added. The resulting reaction mixture was allowed to stir for about 12 h. LC/MS indicated the disappearance of compound AA. Water (10 mL) and ethyl acetate (10 mL) were then added to the reaction mixture. The organic layer was separated, dried ($K_2CO_3$), and the solvent was removed under reduced pressure. The resulting product was purified by column chromatography using a silica gel column eluted with 5% triethylamine, 25% ethyl acetate, and 70% hexane to provide 400 mg of Compound AR as an oil (71% yield). Compound AR was shown to be greater than 97% pure by HPLC analysis.

The identity of Compound AR was confirmed using $^1$H NMR and MS analysis.

$^1$H NMR (CDCl$_3$): δ 1.3 (t, 3H), 1.5 (d, 2H), 2.2 (m, 2H), 2.3 (bs, 3H), 2.4–2.6 (m, 4H), 2.7 (m, 2H), 2.7–2.8 (m, 4H), 3.0 (bs, 3H), 3.7 (m, 2H), 4.2 (q, 2H), 4.7 (s, 2H), 6.9 (m, 3H), 7.3 (m, 4H), 7.4 (m, 4H), 7.45 (m, 4H). MS: m/z 597.

Compound AT was prepared by dissolving Compound AR (0.5 mmol) in 3 mL of methanol and 40 mL of 40% aqueous potassium hydroxide and heating the resulting mixture at 80° C. with stirring for about 2 h. LC/MS indicated disappearance of Compound AT. After completion of the reaction, 2 mL of water and 2 mL of 3N HCl was added to the mixture to adjust the pH to a value of about 1. The resulting precipitate was collected and dried under vacuum to provide 110 mg of Compound AT. Compound AT was shown to be greater than 97% pure by HPLC analysis.

The identity of Compound AT was confirmed using $^1$H NMR and MS analysis.

$^1$H NMR (CDCl$_3$): δ 1.6 (d, 2H), 2.3 (s, 3H), 2.6 (m, 2H), 2.7 (m, 4H), 3.0 (s, 3H), 3.3 (m, 4H), 3.7 (m, 4H), 4.7 (s, 2H), 6.8 (m, 1H), 7.0 (m, 2H), 7.2 (m, 2H), 7.3 (m, 10H), 11.5 (bs, 1H). MS: m/z 569.

5.8 Example 8

Synthesis of Compound AH

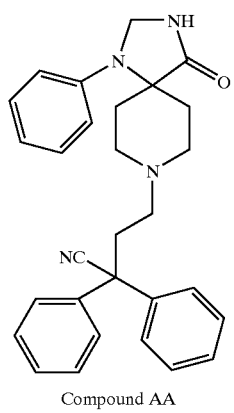

Compound AA

+

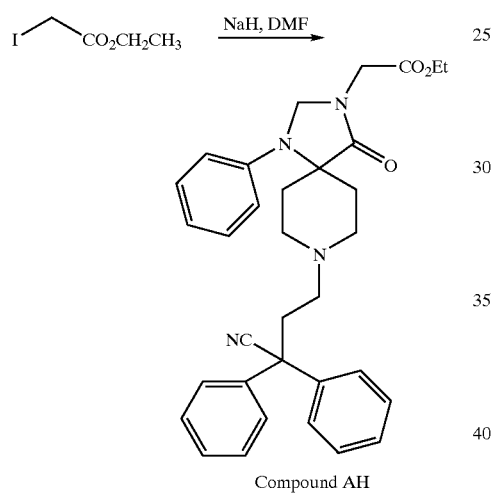

Compound AH 450 mg (1 mmol) of Compound AA were added to about 1.2 mmol of NaH (that had been washed twice with THF) in 10 mL of DMF. Gas evolution occurred and, after 2 min., 1.1 eq. of ethyl iodoacetate acid (1.1 mmol) (commercially available from Sigma-Aldrich, St. Louis, Mo., www.sigma-aldrich.com) was added. The resulting reaction mixture was allowed to stir for about 12 h. LC/MS indicated the disappearance of Compound AA. Water (10 mL) and ethyl acetate (10 mL) were added to the reaction mixture. The organic layer was separated, dried ($K_2CO_3$), and the solvent was removed under reduced pressure. The resulting product was purified by column chromatography using a silica gel column eluted with 5% triethylamine, 25% ethyl acetate, and 70% hexane to provide 390 mg of Compound AH as an oil (72.7% yield). Compound AH was shown to be greater than 94% pure by HPLC analysis.

The identity of Compound AH was confirmed using $^1$H NMR and MS analysis.

$^1$H NMR (CDCl$_3$): δ 1.3 (t, 3H), 1.7 (d, 2H), 2.5–2.65 (m, 6H), 2.75 (m, 2H), 2.85 (m, 2H), 4.1 (s, 2H), 4.2 (m, 2H), 4.75 (s, 2H), 6.85–6.95 (m, 3H), 7.2–7.4 (m, 12H). MS: m/z 537.

5.9 Example 9

Synthesis of Compound AD

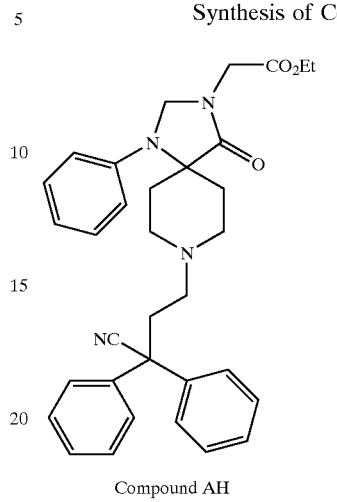

Compound AH

KOH →

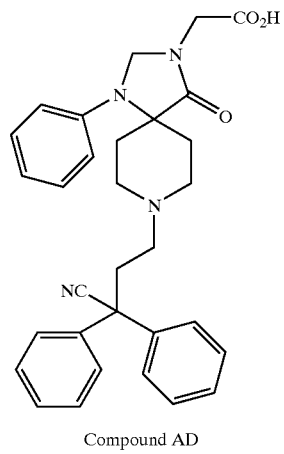

Compound AD

A solution of Compound AH (0.5 mmol) in 3 mL of methanol and 1 mL of 40% aqueous KOH was stirred and heated at 80° C. for about 2 h. LC/MS showed disappearance of Compound AH. After 2 h, 2 mL of water and 2 mL of 3N HCl were added to the mixture to adjust the pH to a value of about 1. The resulting precipitate was isolated by filtration and dried under high vacuum to provide 130 mg of Compound AD (51.2% yield). Compound AD was shown to be greater than 97% pure by HPLC analysis.

The identity of Compound AD was confirmed using $^1$H NMR and MS analysis.

$^1$H NMR (CD$_3$OD): 67 2.2 (d, 2H), 2.7 (m, 2H), 3.0 (m, 2H), 3.2 (m, 2H), 3.6 (m, 2H), 3.8 (m, 2H), 4.2 (s, 2H), 7.0 (m, 1H), 7.1 (m, 2H), 7.3–7.5 (m, 12H). MS: m/z 509.

5.10 Example 10

Synthesis of Compound AG

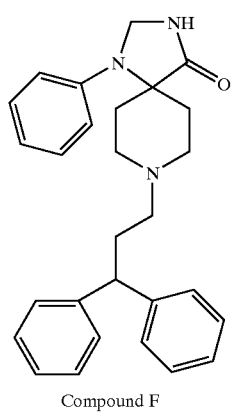

Compound F

+

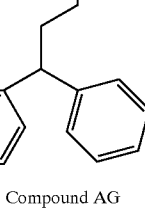

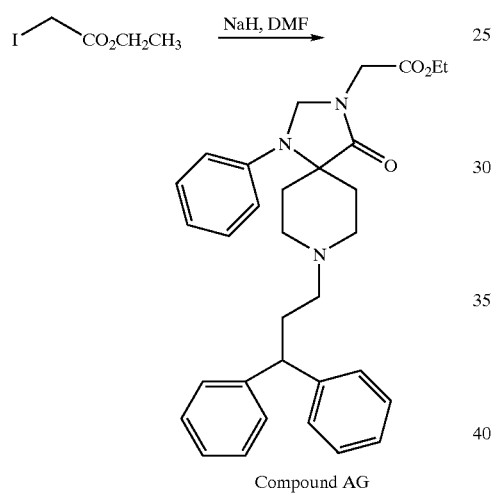

Compound AG 450 mg (1 mmol) of Compound F was added to about 1.2 mmol of NaH (that had been washed twice with THF) in 10 mL of DMF. Gas evolution occurred and, after 2 min., 1.1 eq. of ethyl iodoacetate (1.1 mmol) (commercially available from Sigma-Aldrich, St. Louis, Mo., www.sigma-aldrich.com) was added. The resulting reaction mixture was allowed to stir for about 12 h. LC/MS indicated the disappearance of compound F. Water (10 mL) and ethyl acetate (10 mL) were added to the reaction mixture. The organic layer was separated, dried ($K_2CO_3$), and the solvent was removed under reduced pressure. The resulting product was purified by column chromatography using a silica gel column eluted with 5% triethylamine, 25% ethyl acetate, and 70% hexane) to provide 381 mg of Compound AG as an oil (74.7% yield). Compound AG was shown to be greater than 97% pure by HPLC analysis.

The identity of Compound AG was confirmed using $^1$H NMR and MS analysis.

$^1$H NMR ($CD_3OD$): δ 1.3 (t, 3H), 1.7 (d, 2H), 2.45–2.65 (m, 6H), 2.77 (m, 2H), 2.85 (m, 2H), 4.15 (s, 2H), 4.2 (m, 2H), 4.75 (s, 2H), 6.80–6.95 (m, 3H), 7.2–7.4 (m, 12H). MS: m/z 512.

5.11 Example 11

Synthesis of Compound AE

Compound AG

KOH →

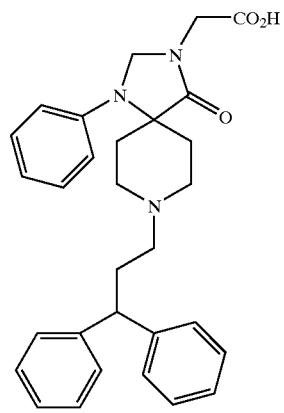

Compound AE

A solution of Compound AG (0.5 mmol) in 3 mL of methanol and 1 mL of 40% aqueous KOH was stirred and heated at 80° C. for about 2 h. LC/MS showed disappearance of Compound AG. After 2 h, 2 mL of water and 2 mL of 3N HCl were added to the mixture to adjust the pH to a value of about 1. The resulting precipitate was isolated by filtration and dried under high vacuum to provide 127 mg of Compound AE (52.5% yield). Compound AE was shown to be greater than 97% pure by HPLC analysis.

The identity of Compound AE was confirmed using $^1$H NMR and MS analysis.

$^1$H NMR ($CD_3OD$): δ 2.1 (d, 2H), 5.5–5.7 (m, 4H), 3.1 (m, 2H), 3.5 (m, 2H), 3.75 (m, 2H), 4.0 (m, 3H), 6.9 (m, 1H), 7.0 (m, 2H), 7.2 (m, 2H), 7.3 (m, 10H). MS: m/z 484.

5.12 Example 12

Synthesis of Compound AM

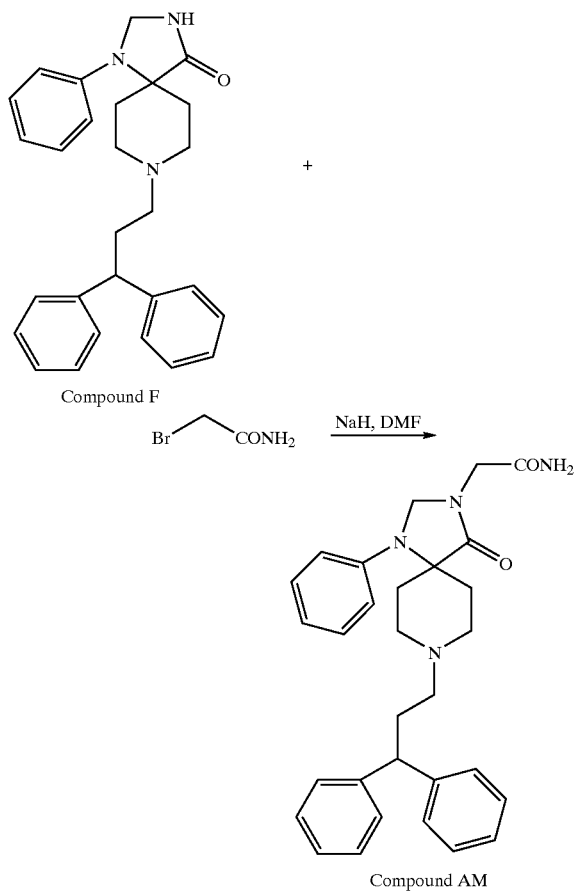

Compound F (0.9 mmol) in 5 mL of DMF was added to a flask containing 1.5 eq. of NaH that had been flushed with argon. 2-Bromoacetamide (1.2 eq.) (commercially available from Sigma-Aldrich, St. Louis, Mo., www.sigma-aldrich.com) was added to the flask and the resulting mixture was allowed to stir at room temperature for 30 min. The mixture was then heated to 60° C. and allowed to stir for about 12 h. The reaction mixture was then cooled to room temperature, diluted with 30 mL of ethyl acetate, and washed with water (10 mL, 2 times). The organic layer was separated, dried (MgSO$_4$), and the solvent removed under reduced pressure to provide a residue that was purified using a florisil column eluted with a mixture of 2% saturated aqueous NH$_4$OH, 28% methanol and 70% methylene chloride to provide 15 mg of Compound AM as a pale yellow solid. Compound AM was shown to be greater than 97% pure by HPLC analysis.

The identity of Compound AM was confirmed using $^1$H NMR and MS analysis.

$^1$H NMR (CDCl$_3$): δ 1.7 (d, 2H), 2.25 (m, 2H), 2.4 (m, 2H), 2.5 (m, 2H) 2.8 (m, 4H), 4.0 (t, 1H), 4.05 (s, 2H), 4.8 (s, 2H), 5.4 (bs, 1H), 6.0 (bs, 1H), 6.95 (m, 3H), 7.2 (m, 2H), 7.3 (m, 10H). MS: m/z 483.3.

5.13 Example 13

Synthesis of Compound AL

Compound AL was synthesized according to the method of Example 10 except that BrCH$_2$CH$_2$NHSO$_2$CH$_3$ was used in place of ethyl iodoacetate. BrCH$_2$CH$_2$NHSO$_2$CH$_3$ can be prepared by reacting from 2-bromoethylamine (commercially available from Sigma-Aldrich, St. Louis, Mo., www.sigma-aldrich.com) with methanesulfonyl chloride in methylene chloride in the presence of triethylamine at 0° as shown in the scheme below:

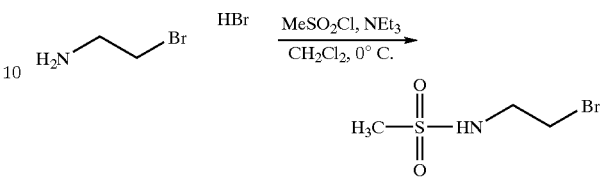

The purity of Compound AL was determined to be greater than 97% by HPLC analysis.

The identity of Compound AL was confirmed using $^1$H NMR and MS analysis.

$^1$H NMR (CD$_3$OD): δ 1.7 (m, 2H), 2.3 (m, 2H), 2.4 (m, 2H) 2.5–2.6 (m, 2H), 2.7–2.8 (m, 4H), 3.0 (s, 3H), 3.4 (m, 2H), 3.6 (m, 2H), 4.0 (t, 1H), 4.8 (s, 2H), 5.1 (bs, 1H), 6.9 (m, 3H), 7.2 (m, 2H), 7.3 (m, 10H). MS: m/z 547.

5.14 Example 14

Synthesis of Compounds AN and AO

Compound AN and Compound AO were synthesized according to the methods of Example 10 and Example 11 except that ethyl 3-iodopropionate and ethyl 5-bromovalerate (each commercially available from Sigma-Aldrich, St. Louis, Mo., www.sigma-aldrich.com), respectively, were used in place of ethyl iodoacetate. The purity of Compound AN and Compound AO was each determined to be greater than 97% by HPLC analysis.

The identity of Compound AN was confirmed using $^1$H NMR and MS analysis.

$^1$H NMR (CDCl$_3$): δ 1.3 (m, 3H), 2.4 (m, 2H), 2.7–2.9 (m, 5H), 3.1 (m, 4H), 3.3 (m, 2H), 3.65 (m, 2H), 3.9 (t, 1H), 4.7 (s, 2H), 6.6 (m, 3H), 7.0 (m, 2H), 7.2 (m, 5H), 7.3 (m, 3H). MS: m/z 498.

The identity of Compound AO was confirmed using $^1$H NMR and MS analysis.

$^1$H NMR (CDCl$_3$): δ 1.5–1.7 (m, 6H), 2.3 (m, 4H), 2.4–3.1 (m, 8H), 3.4 (m, 2H), 3.9 (t, 1H), 4.6 (s, 2H), 6.6–6.8 (m, 2H), 7.1–7.3 (m, 13H). MS: m/z 526.

5.15 Example 15

Synthesis of Compound AP

Compound AP was synthesized according to the method of Example 6 except that ethyl 5-bromovalerate (commercially available from Sigma-Aldrich, St. Louis, Mo., www.sigma-aldrich.com) was used in place of ethyl 3-bromopropionate. The purity of Compound AP was determined to be greater than 97% by HPLC analysis.

The identity of Compound AP was confirmed using $^1$H NMR and MS analysis.

$^1$H NMR (CD$_3$OD): δ 1.7 (m, 7H), 2.3 (s, 3H), 2.4 (m, 2H), 2.7–2.9 (m, 4H), 3.0 (s, 3H), 3.4–3.5 (m, 5H), 3.8 (m, 2H), 4.7 (s, 3H), 6.9 (t, 1H), 7.15 (m, 2H), 7.3–7.4 (m, 12H). MS: m/z 597.

5.16 Example 16

Synthesis of Compound AQ

Compound AQ was synthesized according to the method of Example 6 except that methyl bromoacetate (commercially available from Sigma-Aldrich, St. Louis, Mo., www.sigma-aldrich.com) was used in place of ethyl 3-bromopropionate. The purity of Compound AQ was determined to be greater than 97% by HPLC analysis.

The identity of Compound AQ was confirmed using $^1$H NMR and MS analysis.

$^1$H NMR (CDCl$_3$): δ 1.9 (bs, 2H), 2.2 (m, 2H), 2.3 (bs, 3H), 2.4–2.6 (m, 4H), 2.7 (m, 4H), 3.0 (bs, 3H), 3.7 (s, 3H), 4.1 (s, 2H), 4.7 (s, 2H), 6.9 (m, 3H), 7.3 (m, 4H), 7.3–7.5 (m, 8H). MS: m/z 569.

5.17 Example 17

Synthesis of Compound AS

Compound AS was synthesized according to the method of Example 8 except that ethyl 5-bromovalerate (commercially available from Sigma-Aldrich, St. Louis, Mo., www.sigma-aldrich.com) was used in place of ethyl iodoacetate. The purity of Compound AS was determined to be greater than 97% by HPLC analysis.

The identity of Compound AS was confirmed using $^1$H NMR and MS analysis.

$^1$H NMR (CDCl$_3$): δ 1.3 (t, 3H), 1.7 (m, 8H), 2.3 (m, 2H), 2.5–2.9 (m, 7H), 3.4 (m, 3H), 4.2 (q, 2H), 4.7 (s, 2H), 6.9 (m, 3H), 7.2–7.5 (m, 12H). MS: m/z 579.

5.18 Example 18

Synthesis of Compound AU

Compound AU was synthesized according to the method of Example 9 except that Compound AS (prepared according to the method of Example 17) was used in place of Compound AH. The purity of Compound AU was determined to be greater than 97% by HPLC analysis.

The identity of Compound AU was confirmed using 1H NMR and MS analysis.

$^1$H NMR (CDCl$_3$): δ 1.6–1.8 (m, 6H), 2.4 (m, 2H), 3.1–3.3 (m, 4H), 3.5 (m, 6H), 3.7 (2H), 4.7 (s, 2H), 6.9 (m, 1H), 7.1 (m, 2H), 7.2–7.6 (m, 12H). MS: m/z 551.

5.19 Example 19

Synthesis of Compound AV

Compound AV was synthesized according to the method of Example 9 except that Compound G, shown below:

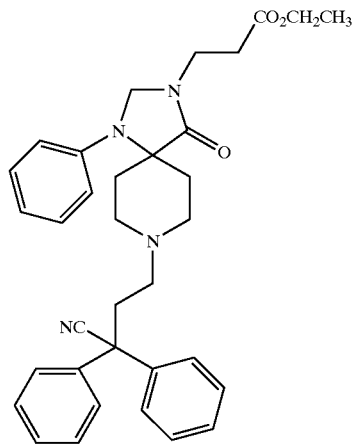

Compound G was used in place of Compound AH.

Compound G was prepared according to the method of Example 8 except that 3-iodopropionate (commercially available from Sigma-Aldrich, St. Louis, Mo., www.sigma-aldrich.com) was used in place of ethyl iodoacetate. The purity of Compound AV was determined to be greater than 97% by HPLC analysis.

The identity of Compound AV was confirmed using $^1$H NMR and MS analysis.

$^1$H NMR (CD$_3$OD): δ 2.0 (d, 2H), 2.7 (m, 4H), 3.0 (m, 2H), 3.2 (m, 2H), 3.6 (m, 2H), 3.7 (m, 2H), 3.8 (m, 2H), 4.8 (s, 2H), 6.9 (m, 1H), 7.0 (m, 2H), 7.3–7.5 (m, 12H). MS: m/z 523.

5.20 Example 20

Synthesis of Compound AI

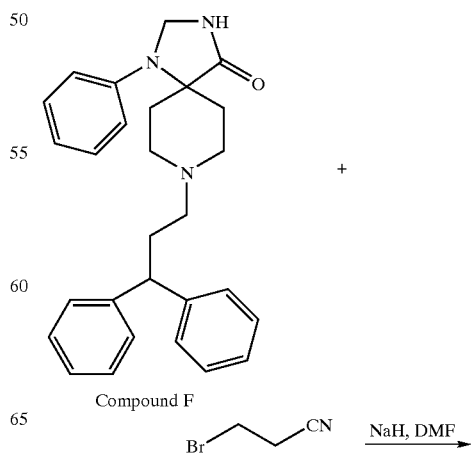

Compound F

-continued

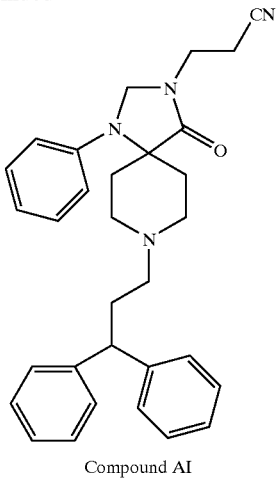

Compound AI

A solution of Compound F (0.9 mmol) in 10 mL of DMF was added to a flask containing 1.5 eq. of NaH (1.4 mmol) that had been flushed with argon and the resulting mixture was allowed to stir at room temperature for about 15 min. 3-Bromopropionitrile (1.2 eq.) (commercially available from Sigma-Aldrich, St. Louis, Mo., www.sigma-aldrich.com) was added to the flask and the resulting mixture allowed to stirr at room temperature for 30 min. The mixture was then heated to 80° C. and allowed to stir for about 12 h. The reaction mixture was then cooled to room temperature, diluted with 10 mL of ethylacetate, and washed with water (10 mL, 2 times). The organic layer was separated, dried (MgSO$_4$), and the solvent removed under reduced pressure to provide a residue that was purified using a silica gel column eluted with 10% triethylamine, 40% ethyl acetate, 50% hexanes to provide Compound AI.

5.21 Example 21

Synthesis of Compound AJ

Compound AJ was synthesized according to the method of Example 20 except that 4-bromobutyronitrile (commercially available from Sigma-Aldrich, St. Louis, Mo., www.sigma-aldrich.com) was used in place of 3-bromopropionitrile.

5.22 Example 22

$\mu$- and ORL-1-Receptor-Binding Affinity Assays 5.22.1 Materials and Methods

ORL-1 Receptor Membrane Preparation

All reagents were from obtained from Sigma (St. Loius, Mo.) unless noted otherwise. Membranes from recombinant HEK-293 cells expressing the human opioid receptor-like (ORL-1) receptor (Perkin Elmer, Boston, Mass.) were prepared by lysing cells in ice-cold hypotonic buffer (2.5 mM MgCl$_2$, 50 mM HEPES, pH 7.4) (10 mL/10 cm dish), followed by homogenization with a tissue grinder/teflon pestle. Membranes were collected by centrifugation at 30,000×g for 15 min at 4° C., and pellets were resuspended in hypotonic buffer to a final concentration of 1–3 mg/mL. Protein concentrations were determined using the BioRad (Hercules, Calif.) protein assay reagent with bovine serum albumen as standard. Aliquots of the ORL-1 receptor membranes were stored at −80° C.

$\mu$- and ORL-1-Receptor-Binding-Assay Procedures

Radioligand dose-displacement binding assays for ORL-1 and A receptors used 0.1 nM [$^3$H]-nociceptin or 0.2 n-M [$^3$H]-diprenorphine (NEN, Boston, Mass.), respectively, with 5–20 mg membrane protein/well in a final volume of 500 ml binding buffer (10 mM MgCl$_2$, 1 mM EDTA, 5% DMSO, 50 mM HEPES, pH 7.4). Reactions were carried out in the absence or presence of increasing concentrations of unlabled nociceptin (American Peptide Company, Sunnyvale, Calif.) or naloxone, for ORL-1 and $\mu$, respectively. All reactions were conducted in 96-deep well polypropylene plates for 1–2 h at room temperature. Binding reactions were terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed performing by three filtration washes with 500 mL of ice-cold binding buffer. Filter plates were subsequently dried at 50° C. for 2–3 h. BetaScint scintillation cocktail (Wallac, Turku, Finland) was added (50 ml/well), and plates were counted using a Packard Top-Count for 1 min/well. The data were analyzed using the one-site competition curve fitting functions in GraphPad PRISM v. 3.0 (San Diego, Calif.).

5.22.2 Results: $\mu$-Receptor-Binding Assay

Generally, the lower the Ki value, the more effective the Triazospiro Compounds are at treating or preventing pain. Typically, the Triazaspiro Compounds have a Ki (nM) of about 300 or less for binding to $\mu$-opioid receptors. In one embodiment, the Triazaspiro Compounds have a Ki (nM) of about 100 or less. In another embodiment, the Triazaspiro Compounds have a Ki (nM) of about 10 or less. In still another embodiment, the Triazaspiro Compounds have a Ki (nM) of about 1 or less. In still another embodiment, the Triazaspiro Compounds have a Ki (nM) of about 0.1 or less.

For example, Compound AG, an illustrative Triazaspiro Compound, binds to $\mu$-opioid receptors with a binding constant Ki of 2.9 nM. Accordingly, the above-disclosed assay indicates that the Triazaspiro Compounds would be useful for treating or preventing pain in an animal.

5.22.3 Results: ORL-1-Receptor-Binding Assay

Generally, the lower the Ki value, the more effective the Triazospiro Compounds are at treating or preventing pain. Typically, the Triazaspiro Compounds have a Ki (nM) of about 10,000 or less for ORL-1 receptors. In one embodiment, the Triazaspiro Compounds have a Ki (nM) of about 2000 or less. In another embodiment, the Triazaspiro Compounds have a Ki (nM) of about 1000 or less. In still another embodiment, the Triazaspiro Compounds have a Ki (nM) of about 100 or less. In still another embodiment, the Triazaspiro Compounds have a Ki (nM) of about 10 or less.

For example, Compound AG, an illustrative Triazaspiro Compound, binds to ORL-1 receptors with a binding constant Ki of 18 nM. Accordingly, the above-disclosed assay indicates that the Triazaspiro Compounds would be useful for treating or preventing pain in an animal.

5.23 Example 23

$\mu$- and ORL-1-Opioid Receptor $\gamma$S Functional Activity 5.23.1 Materials and Methods

[$^{35}$S]GTPgS functional assays were conducted using freshly thawed ORL-1 or $\mu$-receptor membranes, as appropriate. Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.066 mg/mL for ORL-1 receptor and 0.026 mg/mL for it-receptor), saponin (10 mg/ml), GDP (3 mM) and [$^{35}$S]GTPgS (0.20 nM; NEN).

The prepared membrane solution (190 mL/well) was transferred to 96-shallow well polypropylene plates containing 10 mL of 20× concentrated stock solutions of the agonist nociceptin prepared in dimethyl sulfoxide ("DMSO"). Plates were incubated for 30 min at room temperature with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 mL of ice-cold binding buffer (10 mM $NaH_2PO_4$, 10 mM $Na_2HPO_4$, pH 7.4). Filter plates were subsequently dried at 50° C. for 2–3 h. BetaScint scintillation cocktail (Wallac, Turku, Finland) was added (50 mL/well) and plates were counted using a Packard Top-Count for 1 min/well. Data were analyzed using the sigmoidal dose-response curve fitting functions in GraphPad PRISM, v. 3.0.

5.23.2 Results: μ-Receptor Function

μ GTP $EC_{50}$ is the concentration of a compound providing 50% of the maximal response for the compound at μ receptor. Triazaspiro Compounds typically having a μ GTP $EC_{50}$ (nM) of about 5000 or less stimulate it opioid receptor function. In one embodiment, the Triazaspiro Compounds have a μ GTP $EC_{50}$ (nM) of about 1000 or less. In still another embodiment, the Triazaspiro Compounds have a μ GTP $EC_{50}$ (nM) of about 100 or less. In still another embodiment, the Triazaspiro Compounds have a μ GTP $EC_{50}$ (nM) of about 10 or less. In still another embodiment, the Triazaspiro Compounds have a μ GTP $EC_{50}$ (nM) of about 1 or less. In still another embodiment, the Triazaspiro Compounds have a μ GTP $EC_{50}$ (rAM) of about 0.1 or less.

μ GTP Emax % is the maximal effect elicited by a compound relative to the effect elicited by [D-Ala2, N-methyl-Phe4, Gly-ol5]-enkephalin ("DAMGO"), a standard μ agonist. Generally, the μ GTP Emax (%) value measures the efficacy of a compound to treat or prevent pain. Typically the Triazaspiro Compounds have a μ GTP Emax (%) of greater than 50%. In one embodiment the Triazaspiro Compounds have a μ GTP Emax (%) of greater than 75%. In still another embodiment the Triazaspiro Compounds have a μ GTP Emax (%) of greater than 88%. In still another embodiment the Triazaspiro Compounds have a μ GTP Emax (%) of greater than 100%.

For example, Compound AG, an illustrative Triazaspiro Compound, stimulates μ-opioid-receptor function and exhibits a μ GTP $EC_{50}$ of 44 nM and a μ GTP Emax of 88%. Accordingly, this assay indicates that Triazaspiro Compounds would be useful useful for treating or preventing pain in an animal.

5.23.3 Results: ORL-1-Receptor Function

ORL-1 GTP $EC_{50}$ is the concentration of a compound providing 50% of the maximal response for the compound at an ORL-1 receptor. Triazaspiro Compounds having a ORL-1 GTP $EC_{50}$ (nM) of about 10,000 or less stimulate ORL-1 opioid-receptor function. In one embodiment, the Triazaspiro Compounds have a ORL-1 GTP $EC_{50}$ (nM) of about 1000 or less. In still another embodiment, the Triazaspiro Compounds have a ORL-1 GTP $EC_{50}$ (nM) of about 100 or less. In still another embodiment, the Triazaspiro Compounds have a ORL-1 GTP $EC_{50}$ (nM) of about 50 or less. In still another embodiment, the Triazaspiro Compounds have a ORL-1 GTP $EC_{50}$ (nM) of about 10 or less.

ORL-1 GTP Emax % is the maximal effect elicited by a compound relative to the effect elicited by nociceptin, a standard ORL-1 agonist. Generally, the ORL-1 GTP Emax (%) value measures the efficacy of a compound to treat or prevent pain. Typically the Triazaspiro Compounds have a ORL-1 GTP Emax (%) of greater than 50%. In one embodiment the Triazaspiro Compounds have a ORL-1 GTP Emax (%) of greater than 75%. In still another embodiment the Triazaspiro Compounds have a ORL-1 GTP Emax (%) of greater than 88%. In still another embodiment the Triazaspiro Compounds have a ORL-1 GTP Emax (%) of greater than 100%.

For example, Compound AG, an illustrative Triazaspiro Compound, stimulates ORL-1 opioid-receptor function and exhibits a ORL-1 GTP $EC_{50}$ of 71 nM and a ORL-1 GTP Emax of 95%. Accordingly, these assays indicate that Triazaspiro Compounds would be useful for treating or preventing pain in an animal.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of formula (Ia):

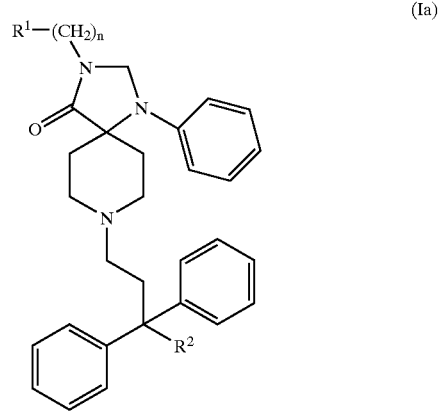

(Ia)

or a pharmaceutically acceptable salt thereof, wherein:

$R^1$ is hydrogen, —COOH, —$COOR^3$, —C(O)$NH_2$, —C(O)NH($C_1$–$C_4$ alkyl), —C(O)N($C_1$–$C_4$ alkyl) ($C_1$–$C_4$ alkyl), —CN, —N(H)S(O)$_2$($C_1$–$C_4$ alkyl), or

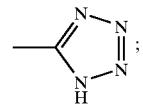

$R^2$ is —COOH, —$COOR^3$ or

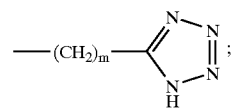

$R^3$ is —($C_1$–$C_6$ alkyl), benzyl, phenyl, or —($C_3$–$C_6$ cycloalkyl);

n is 0 when $R^1$ is hydrogen, and n is an integer ranging from 1 to 4 when $R^1$ is other than hydrogen; and m is an integer ranging from 0 to 4.

2. The compound or pharmaceutically acceptable salt of the compound of claim 1, wherein $R^1$ is hydrogen and n is 0.

3. The compound or pharmaceutically acceptable salt of the compound of claim 1, wherein $R^1$ is —COOH or —COOR$^3$.

4. The compound or pharmaceutically acceptable salt of the compound of claim 1, wherein $R^1$ is —C(O)NH$_2$, —C(O)NH(C$_1$–C$_4$ alkyl) or —C(O)N(C$_1$–C$_4$ alkyl)(C$_1$–C$_4$ alkyl).

5. The compound or pharmaceutically acceptable salt of the compound of claim 1, wherein $R^1$ is —CN.

6. The compound or pharmaceutically acceptable salt of the compound of claim 1, wherein $R^1$ is —N(H)S(O)$_2$(C$_1$–C$_4$ alkyl).

7. The compound or pharmaceutically acceptable salt of the compound of claim 1, wherein $R^1$ is

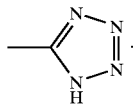

8. The compound or pharmaceutically acceptable salt of the compound of claim 1, wherein $R^2$ is —COOH or —COOR$^3$.

9. The compound or pharmaceutically acceptable salt of the compound of claim 1, wherein $R^2$ is

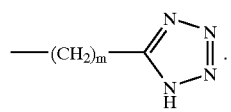

10. The compound or pharmaceutically acceptable salt of the compound of claim 1, where m is 0 or 1.

11. The compound or pharmaceutically acceptable salt of the compound of claim 1, whererin m is 0.

12. The compound of claim 1 having the structure:

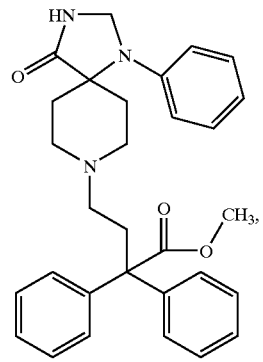

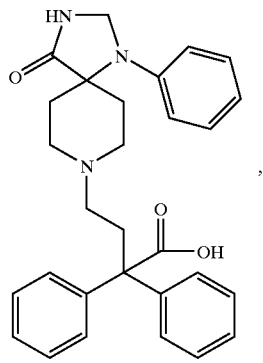

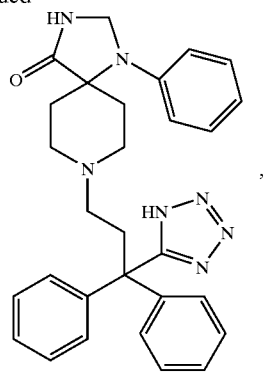

or a pharmaceutically acceptable salt thereof.

13. A composition comprising an effective amount of a compound or a pharmaceutically acceptable salt of the compound of claim 1 and a pharmaceutically acceptable carrier or excipient.

14. The composition of claim 13, further comprising an opioid analgesic.

15. The composition of claim 13, further comprising a non-opioid analgesic.

16. The composition of claim 13, further comprising an anti-emetic agent.

17. A compound of formula (Ib):

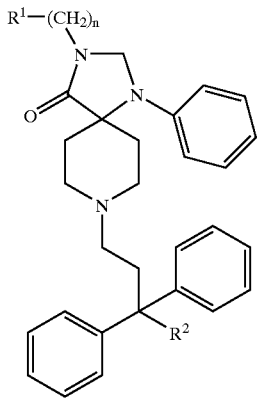

(Ib)

or a pharmaceutically acceptable salt thereof, wherein:

$R^1$ is —COOH, —COOR$^3$, —C(O)NH$_2$, —C(O)NH(C$_1$–C$_4$ alkyl), —C(O)N(C$_1$–C$_4$ alkyl)(C$_1$–C$_4$ alkyl), —CN, —N(H)S(O)$_2$(C$_1$–C$_4$ alkyl), or

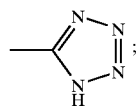

$R^2$ is —COOH, —COOR$^3$, —C(O)N(CH$_3$)$_2$, or

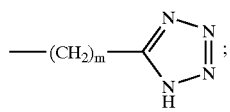

R³ is —(C₁–C₆ alkyl), benzyl, phenyl, or —(C₃–C₆ cycloalkyl);

n is an integer ranging from 1 to 4; and m is an integer ranging from 0 to 4.

18. The compound or a pharmaceutically acceptable salt of the compound of claim 17, wherein R¹ is —COOH or —COOR³.

19. The compound or a pharmaceutically acceptable salt of the compound of claim 17, wherein R¹ is —C(O)NH₂, —C(O)NH(C₁–C₄ alkyl) or —C(O)N(C₁–C₄ alkyl)(C₁–C₄ alkyl).

20. The compound or a pharmaceutically acceptable salt of the compound of claim 17, wherein R¹ is —CN.

21. The compound or a pharmaceutically acceptable salt of the compound of claim 17, wherein R¹ is —N(H)S(O)₂(C₁–C₄ alkyl).

22. The compound or a pharmaceutically acceptable salt of the compound of claim 17, wherein R¹ is

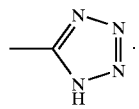

23. The compound or a pharmaceutically acceptable salt of the compound of claim 17, wherein R² is —COOH or —COOR³.

24. The compound or pharmaceutically acceptable salt of the compound of claim 17, whererin m is 0 or 1.

25. The compound or pharmaceutcially acceptable salt of the compound of claim 17, wherein m is 0.

26. The compound or a pharmaceutically acceptable salt of the compound of claim 17, wherein R² is —C(O)N(CH₃)₂.

27. The compound or a pharmaceutically acceptable salt of the compound of claim 17, wherein R² is

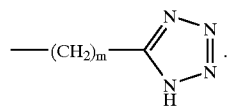

28. The compound of claim 17 having the structure:

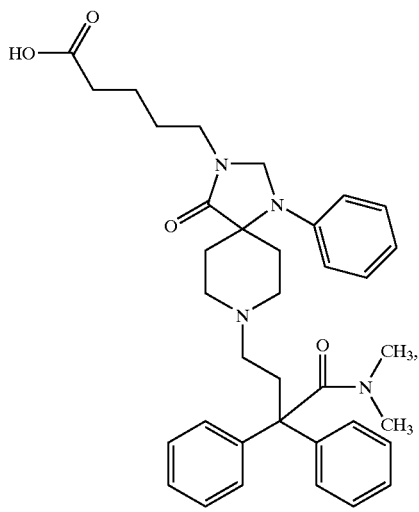

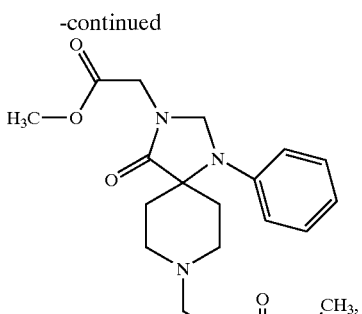

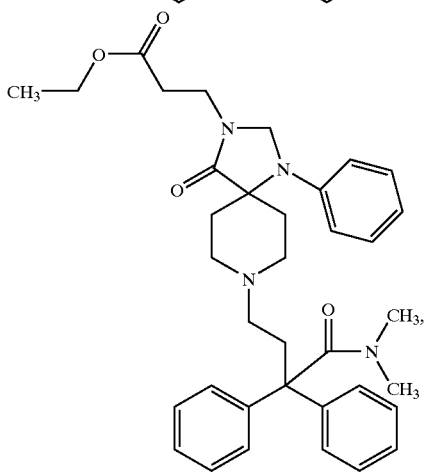

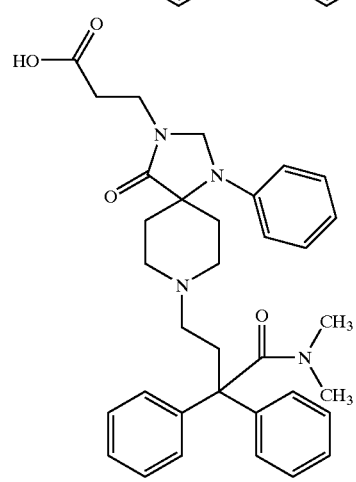

or a pharmaceutically acceptable salt thereof.

29. A composition comprising an effective amount of a compound or a pharmaceutically acceptable salt of the compound of claim 17 and a pharmaceutically acceptable carrier or excipient.

30. The composition of claim 29, further comprising an opioid analgesic.

31. The composition of claim 29, further comprising a non-opioid analgesic.

32. The composition of claim 29, further comprising an anti-emetic agent.

33. A compound of formula (Ic):

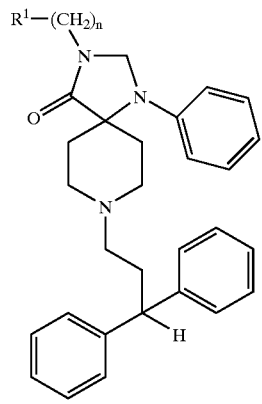

(Ic)

or a pharmaceutically acceptable salt thereof, wherein:

$R^1$ is —COOH, —C(O)NH$_2$, —C(O)NH(C$_1$–C$_4$ alkyl), —C(O)N(C$_1$–C$_4$ alkyl)(C$_1$–C$_4$ alkyl), —N(H)S(O)$_2$(C$_1$–C$_4$ alkyl), or

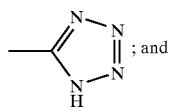 ; and n is an integer ranging from 1 to 4.

34. The compound of claim 33, whererin n is 2.

35. The compound of claim 33, wherein n is 1.

36. The compound or a pharmaceutically acceptable salt of the compound of claim 33, wherein $R^1$ is —COOH.

37. The compound or a pharmaceutically acceptable salt of the compound of claim 33, wherein $R^1$ is —C(O)NH$_2$, —C(O)NH(C$_1$–C$_4$ alkyl) or —C(O)N(C$_1$–C$_4$ alkyl)(C$_1$–C$_4$ alkyl).

38. The compound or a pharmaceutically acceptable salt of the compound of claim 33, wherein $R^1$ is —N(H)S(O)$_2$(C$_1$–C$_4$ alkyl).

39. The compound or a pharmaceutically acceptable salt of the compound of claim 33, wherein $R^1$ is

40. The compound of claim 33 selected from the group consisting of:

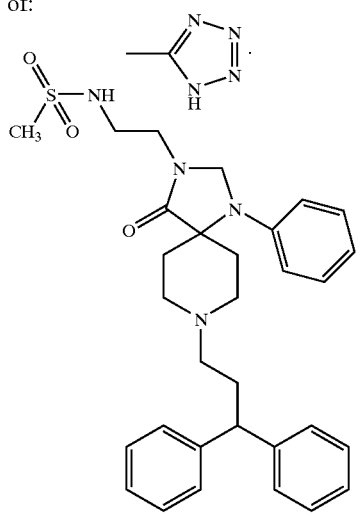

-continued

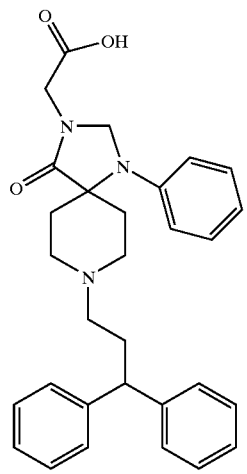

,

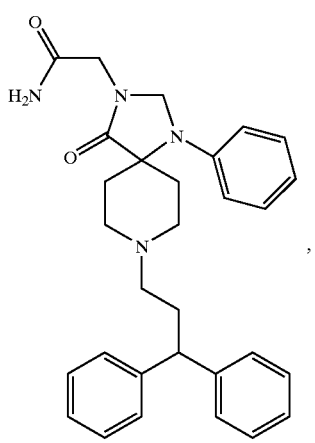

,

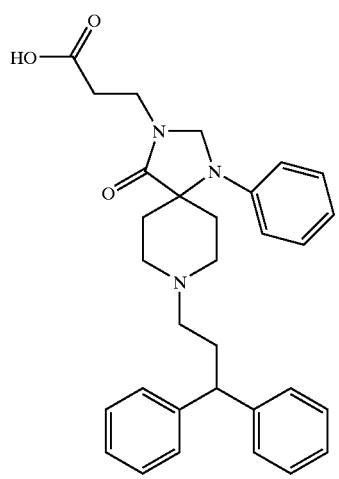

,

-continued

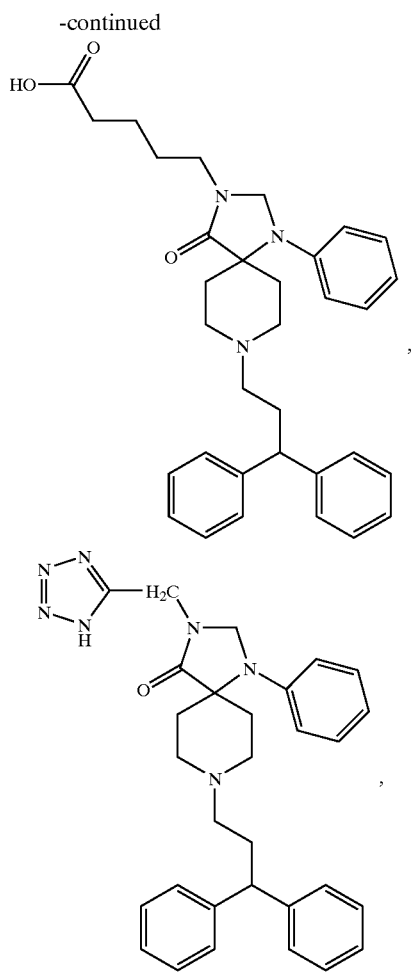

,

-continued

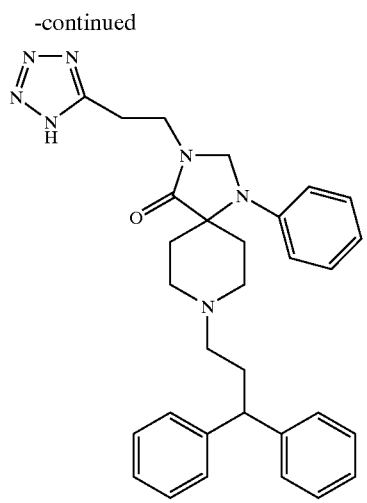

or a pharmaceutically acceptable salt thereof.

41. A composition comprising an effective amount of a compound or a pharmaceutically acceptable salt of the compound of claim 33 and a pharmaceutically acceptable carrier or excipient.

42. The composition of claim 41, further comprising an opioid analgesic.

43. The composition of claim 41, further comprising a non-opioid analgesic.

44. The composition of claim 41, further comprising an anti-emetic agent.

* * * * *